(12) United States Patent
Ren et al.

(10) Patent No.: US 9,859,506 B2
(45) Date of Patent: Jan. 2, 2018

(54) ORGANIC ELECTROLUMINESCENT COMPOUND AND ORGANIC PHOTOELECTRIC APPARATUS THEREOF

(71) Applicants: Shanghai Tianma AM-OLED Co., Ltd, Shanghai (CN); Tianma Micro-electronics Co., Ltd., Shenzhen (CN)

(72) Inventors: Hongyang Ren, Shanghai (CN); Xiangcheng Wang, Shanghai (CN); Wei He, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 15/163,899

(22) Filed: May 25, 2016

(65) Prior Publication Data

US 2017/0186972 A1    Jun. 29, 2017

(30) Foreign Application Priority Data

Dec. 25, 2015 (CN) .......................... 2015 1 0993503

(51) Int. Cl.
*B32B 19/00* (2006.01)
*H01L 51/00* (2006.01)
(Continued)

(52) U.S. Cl.
CPC ........ *H01L 51/0072* (2013.01); *C07D 487/14* (2013.01); *C09K 11/02* (2013.01); *C09K 11/06* (2013.01); *H01L 51/0071* (2013.01); *H01L 51/5004* (2013.01); *C09K 2211/1007* (2013.01); *C09K 2211/1044* (2013.01); *H01L 51/001* (2013.01); *H01L 51/5012* (2013.01); *H01L 51/56* (2013.01); *H01L 2251/552* (2013.01)

(58) Field of Classification Search
CPC ............. H01L 51/0072; H01L 51/0071; H01L 51/5004; H01L 51/001; H01L 51/5012; H01L 51/56; H01L 2251/552; C07D 487/14; C09K 11/02; C09K 11/06; C09K 2211/1007; C09K 2211/1044
USPC ......................................................... 428/690
See application file for complete search history.

(56) References Cited

U.S. PATENT DOCUMENTS

2016/0093813 A1*   3/2016   Stoessel ................ C09K 11/06
                                                                                    257/40

FOREIGN PATENT DOCUMENTS

CN      103443949 A      12/2013
CN      103694992 A      4/2014
(Continued)

OTHER PUBLICATIONS

Shoji Matsumoto et al., Novel formation of diimidazo[1,2-a:2',1'-c]quinoxaline derivatives and their optical properties, Organic & Biomolecular Chemistry, 2011, pp. 5941-5944.

*Primary Examiner* — Hui H Chin
(74) *Attorney, Agent, or Firm* — Anova Law Group, PLLC

(57) ABSTRACT

A nitrogen-containing heterocyclic compound having a general formula (I) and an organic photoelectric apparatus are provided. The compound of general formula (I) is:

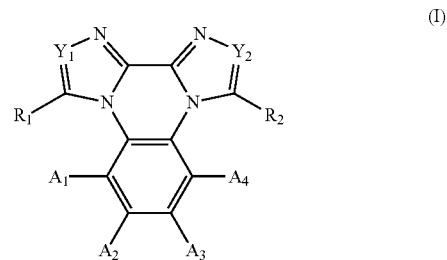

wherein $A_1$ to $A_4$ are independently selected from a hydrogen atom, a function group having a general formula (II); $A_1$ to $A_4$ include at least one function group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N, the general formula (II) being:

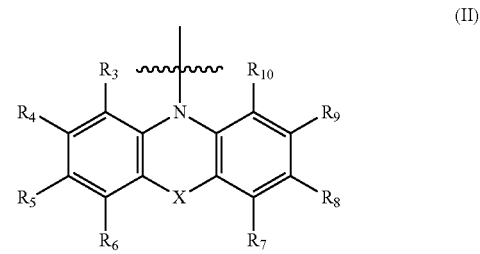

wherein X is selected from one of oxyl group (—O—), sulfhydryl group (—S—), substituted or non-substituted imino group, substituted or non-substituted methylene group, and substituted or non-substituted silicylene group; and $R_3$ to $R_{10}$ are independently selected from one of hydrogen, deuterium, $C_{1-30}$ alkyl group, $C_{6-30}$ aromatic group, and $C_{2-30}$ heterocyclic aromatic group.

20 Claims, 3 Drawing Sheets

(51) Int. Cl.
*H01L 51/50* (2006.01)
*C09K 11/02* (2006.01)
*C09K 11/06* (2006.01)
*C07D 487/14* (2006.01)
*H01L 51/56* (2006.01)

(56) References Cited

FOREIGN PATENT DOCUMENTS

| | | |
|---|---|---|
| CN | 105102581 A | 11/2015 |
| CN | 105102582 A | 11/2015 |
| JP | 2011162694 A | 8/2011 |
| KR | 1020100097797 A | 9/2010 |
| KR | 1020100110495 A | 10/2010 |
| WO | 2015135625 A1 | 9/2015 |

* cited by examiner

ORGANIC ELECTROLUMINESCENT COMPOUND AND ORGANIC PHOTOELECTRIC APPARATUS THEREOF

CROSS-REFERENCES TO RELATED APPLICATIONS

This application claims the priority of Chinese patent application No. 201510993503.8, filed on Dec. 25, 2015, the entirety of which is incorporated herein by reference.

FIELD OF THE INVENTION

The present invention generally relates to the field of organic electroluminescent material and, more particularly, relates to organic electroluminescent materials and their applications in organic photoelectric apparatus.

BACKGROUND

Recently, organic light-emitting diode (OLED) has become a mostly focused new generation of display products because of its self-emitting characteristics, high-efficiency, wide color region, and wide viewing-angles, etc. The organic material used to form the OLED plays a critical role in developing OLED.

When the organic material in a light-emitting layer of an OLED is electrically activated, the singlet excitons ($S_1$) and the triplet excitons ($T_1$) are generated. According to the self-spin statistics, the ratio of the singlet excitons ($S_1$) to the triplet excitons ($T_1$) is 1:3. According to the light-emitting principles, the materials of the light-emitting layer of the OLED include fluorescence materials and phosphorescent materials, etc.

The fluorescent materials are only able to use 25% of singlet excitons (S1), which can be back to the ground state $S_0$ by a radiative transition. Thus, the maximum external efficiency of the OLED using the fluorescent materials as the light-emitting layer is unable to break such a limitation. The phosphorescent materials are able to use not only the 25% of singlet excitons ($S_1$), but also 75% of the triplet excitons (T1). Thus, theoretically, the quantum efficiency of phosphorescence materials is 100%; and they are superior to the fluorescent materials when they are used in the OLED. However, the phosphorescent materials are usually rare complexes, the material cost is relatively high. Further, the blue phosphorescence materials have always been having issues on the efficiency and the lifespan when they are applied in the OLED.

In 2011, professor Adachi at Kyushu University, Japan, reported the thermally activated delayed fluorescence (TADF) material. Such a material presented a relatively good light-emitting performance. The band gap value of the $S_1$ state and the $T_1$ state of the TADF material is relatively small; and the lifespan of the $T_1$ excitons of the TADF material is relatively long. Under a certain temperature condition, the $T_1$ excitons may have a reverse intersystem crossing (RISC) to achieve the $T_1 \rightarrow S_1$ process; and achieve a radiative decay from the $S_1$ state to the ground state $S_0$. Thus, when the TADF material is used as the light-emitting layer in the OLED, the light-emitting efficiency of the OLED may be comparable to that of the OLED using the phosphorescence materials as the light-emitting layer. Further, the TADF material does not need rare metal elements. Thus, the material cost is relatively low.

However, the existing types of TADF materials are limited; and there is a need to develop novel TADF materials with enhanced performance. The disclosed methods and material structures are directed to solve one or more problems set forth above and other problems in the art.

BRIEF SUMMARY OF THE DISCLOSURE

One aspect of the present disclosure includes a nitrogen-containing heterocyclic compound having a general formula (I):

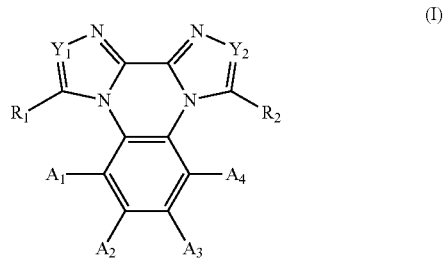

where $A_1$, $A_2$, $A_3$, and $A_4$ are independently selected from a hydrogen atom, a functional group having a general formula (II); $A_1$, $A_2$, $A_3$, and $A_4$ include at least one functional group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N, the general formula (II) being:

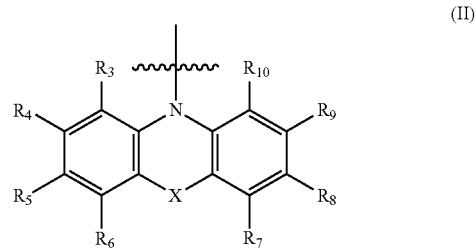

where X is selected from one of oxyl group (—O—), sulfhydryl group (—S—), substituted or non-substituted imino group, substituted or non-substituted methylene group, and substituted or non-substituted silicylene group; and $R_3$, $R_4$, $R_5$, $R_6$, $R_7$, $R_8$, $R_9$, and $R_{10}$ are independently selected from any one of hydrogen, deuterium, $C_{1-30}$ alkyl group, $C_{6-30}$ aromatic group, and $C_{2-30}$ heterocyclic aromatic group.

Another aspect of the present disclosure includes an organic photoelectric apparatus. The organic photoelectric apparatus includes an anode substrate, at least one organic layer formed over the anode substrate, and a cathode formed over the organic layer. The organic layer includes at least one nitrogen-containing heterocyclic compound having a general formula (I):

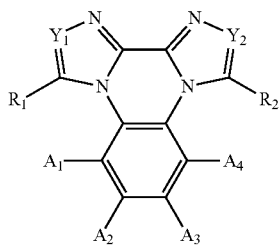

where $A_1$, $A_2$, $A_3$, and $A_4$ are independently selected from a hydrogen atom, a functional group having a general formula (II); and $A_1$, $A_2$, $A_3$, and $A_4$ include at least one functional group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N, the general formula (II) being:

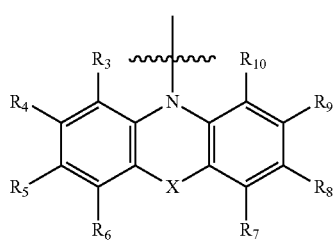

where X is selected from one of oxyl group (—O—), sulfhydryl group (—S—), substituted or non-substituted imino group, substituted or non-substituted methylene group, and substituted or non-substituted silicylene group; and $R_3$, $R_4$, $R_5$, $R_6$, $R_7$, $R_8$, $R_9$, and $R_{10}$ are independently selected from any one of hydrogen, deuterium, $C_{1-30}$ alkyl group, $C_{6-30}$ aromatic group, and $C_{2-30}$ heterocyclic aromatic group.

Another aspect of the present disclosure includes a process for fabricating an organic photoelectric apparatus. The method includes providing an anode substrate; forming at least one organic layer over the anode substrate; and forming a cathode layer over the organic layer, wherein the at least one organic layer includes at least one nitrogen-containing heterocyclic compound having a general formula (I):

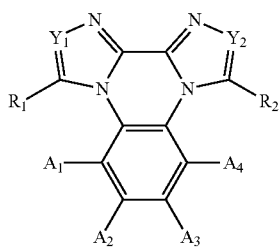

where $A_1$, $A_2$, $A_3$, and $A_4$ are independently selected from a hydrogen atom, a functional group having a general formula (II); and $A_1$, $A_2$, $A_3$, and $A_4$ include at least one functional group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N, the general formula (II) being:

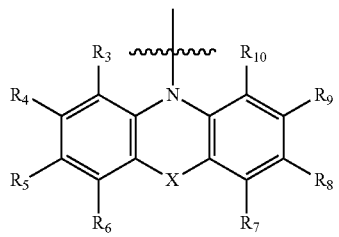

where X is selected from one of oxyl group (—O—), sulfhydryl group (—S—), substituted or non-substituted imino group, substituted or non-substituted methylene group, and substituted or non-substituted silicylene group; and $R_3$, $R_4$, $R_5$, $R_6$, $R_7$, $R_8$, $R_9$, and $R_{10}$ are independently selected from any one of hydrogen, deuterium, $C_{1-30}$ alkyl group, $C_{6-30}$ aromatic group, and $C_{2-30}$ heterocyclic aromatic group.

Other aspects of the present disclosure can be understood by those skilled in the art in light of the description, the claims, and the drawings of the present disclosure.

DETAILED DESCRIPTION

Figure 1:
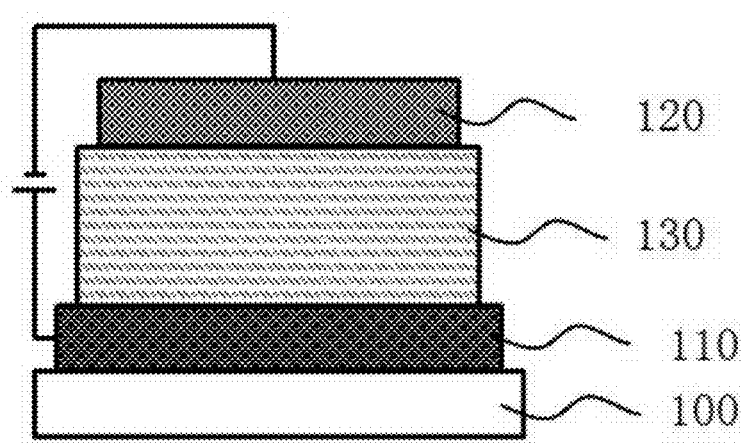
FIG. 1 illustrates an exemplary OLED consistent with the disclosed embodiments.

Reference will now be made in detail to exemplary embodiments of the invention, which are illustrated in the accompanying drawings. Wherever possible, the same reference numbers will be used throughout the drawings to refer to the same or like parts.

According to the disclosed embodiments, a compound of general formula (I) is provided. The general formula (I) may be:

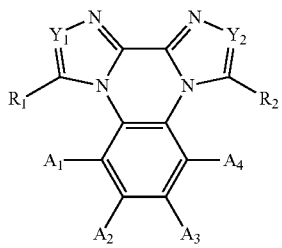

(I)

wherein $A_1$, $A_2$, $A_3$, and $A_4$ may be independently selected from a hydrogen atom, or a compound having a general formula (II). Further, $A_1$, $A_2$, $A_3$, and $A_4$ may include at least one compound having the general formula (II). According to the general formula (II), the disclosed compound may be referred to as a nitrogen-containing heterocyclic compound. $R_1$ and $R_2$ may be independently selected from hydrogen, deuterium, $C_{1-30}$ alkyl group, $C_{6-30}$ aromatic group, and $C_{2-30}$ heterocyclic aromatic group, etc. $Y_1$ and $Y_2$ may be independently selected from substituted or non-substituted carbon or nitrogen, etc.

The compound having the general formula (II) may be:

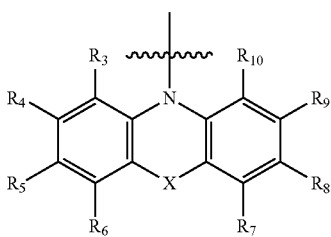

(II)

where X may be selected from oxyl group (—O—), sulfhydryl group (—S—), substituted or non-substituted imino group, substituted or non-substituted methylene group, and substituted or non-substituted silicylene group, etc. $R_3$, $R_4$, $R_5$, $R_6$, $R_7$, $R_8$, $R_9$, and $R_{10}$ may be independently selected from hydrogen, deuterium, $C_{1-30}$ alkyl group, $C_{6-30}$ aromatic group, or $C_{2-30}$ heterocyclic aromatic group, etc.

In one embodiment, the $C_1$-$C_{30}$ alkyl group includes the alkyl group having 1-20 carbon atoms. In certain other embodiments, the $C_1$-$C_{30}$ alkyl group includes the alkyl group having 1-10 carbon atoms. In still certain other embodiments, the $C_1$-$C_{30}$ alkyl group includes the alkyl group having 1-6 carbon atoms.

In one embodiment, the $C_{6-30}$ aromatic group may be the aromatic group having 6-15 carbon atoms. In certain other embodiments, the $C_{6-30}$ aromatic group may be the aromatic group having 6-10 carbon atoms.

In one embodiment, the $C_{2-30}$ aromatic group may be the aromatic group having 2-20 carbon atoms. In certain other embodiments, the $C_{2-30}$ aromatic group may be the aromatic group having 2-10 carbon atoms.

In one embodiment, the oxyl group may be

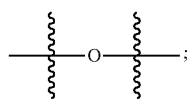 [SMILES: *O*]

the sulfhydryl group may be

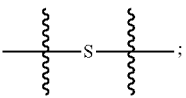

the substituted or non-substituted imino group may be

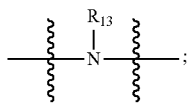

the substituted or non-substituted methylene group may be

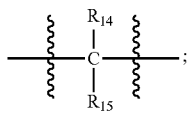

and the substituted or non-substituted silicylene group may be

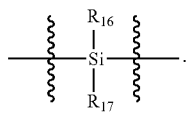

The $R_{13}$, $R_{14}$, $R_{15}$, $R_{16}$, and $R_{17}$ may be independently selected from any one of hydrogen, deuterium, alkyl group, $C_{1-30}$ alkyl group, $C_{6-30}$ aromatic group, or $C_{2-30}$ heterocyclic group, etc.

In one embodiment, the energy level difference ($\Delta E_{st}$) between the lowest singlet state $S_1(E_{s1})$ and the lower triplet state $T_1(E_{T1})$ may be $\Delta E_{st}=E_{s1}-E_{T1} \leq 0.30$ eV, such as 0.29 eV, 0.28 eV, 0.27 eV, 0.26 eV, 0.25 eV, 0.24 eV, 0.23 eV, 0.22 eV, 0.21 eV, 0.20 eV, 0.19 eV, 0.18 eV, 0.17 eV, 0.16 eV, 0.15 eV, 0.14 eV, 0.13 eV, 0.12 eV, 0.11 eV, 0.10 eV, 0.09 eV, 0.08 eV, 0.07 eV, 0.06 eV, 0.05 eV, 0.04 eV, 0.03 eV, 0.02 eV or 0.01 eV, etc. When $\Delta E_{st} \geq 0.30$ eV, the fluorescent delay effect of the compound may not be obvious.

In one embodiment, the $\Delta E_{st}$ of the compound having the general formula (I) is smaller than approximately 0.25 eV. That is, $\Delta E_{st} \leq 0.25$ eV.

In certain other embodiments, the $\Delta E_{st}$ of the compound having the general formula (I) is smaller than approximately 0.15 eV. That is, $\Delta E_{st} \leq 0.15$ eV.

In still certain other embodiments, the $\Delta E_{st}$ of the compound having the general formula (I) is smaller than approximately 0.10 eV. That is, $\Delta E_{st} \leq 0.10$ eV.

In still certain other embodiments, the $\Delta E_{st}$ of the compound having the general formula (I) is smaller than approximately 0.05 eV. That is, $\Delta E_{st} \leq 0.05$ eV.

In still certain other embodiments, the $\Delta E_{st}$ of the compound having the general formula (I) is smaller than approximately 0.02 eV. That is, $\Delta E_{st} \leq 0.02$ eV.

In still certain other embodiments, the $\Delta E_{st}$ of the compound having the general formula (I) is smaller than approximately 0.01 eV. That is, $\Delta E_{st} \leq 0.01$ eV.

Such ranges of $\Delta E_{st}$ of the compound may have obvious fluorescent effect.

In one embodiment, the compound of the general formula (II) may be one or more selected from —O—, —S—, —CH$_2$—, —C(CH$_3$)$_2$—, —CH(CH$_3$)—,

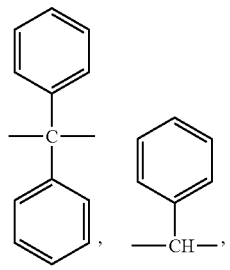

—SiH$_2$—, —Si(CH$_3$)$_2$—, —SiH(CH$_3$)—,

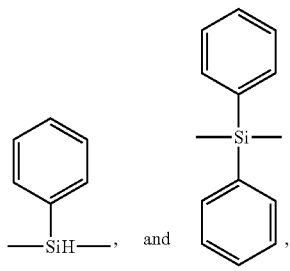

etc.

In certain other embodiments, R$_3$, R$_4$, R$_5$, R$_6$, R$_7$, R$_8$, R$_9$ and R$_{10}$ may all be hydrogen.

In one embodiment, the compound of the general formula (II) may be one or more of

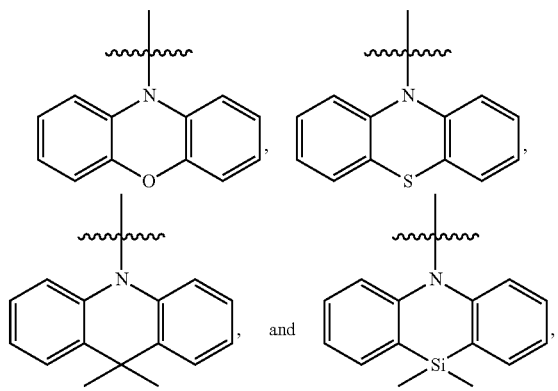

etc.

In one embodiment, the present disclosed nitrogen-containing heterocyclic compound may be one selected from the following compounds 1-64.

1

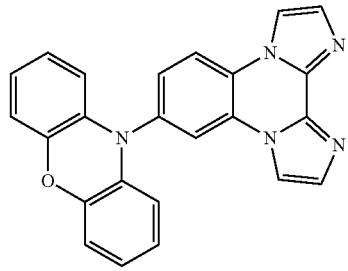

-continued

2

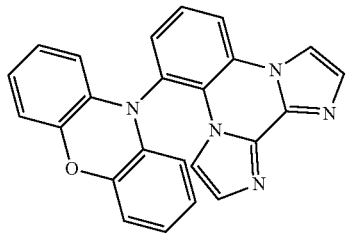

3

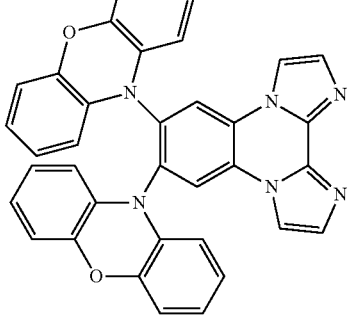

4

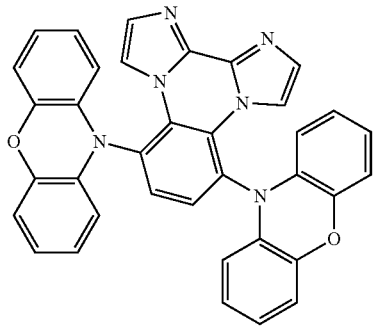

5

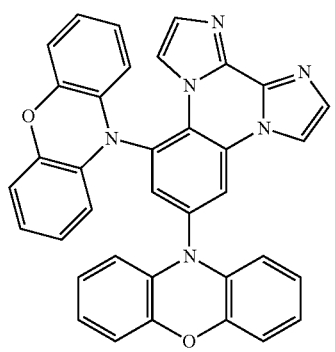

6

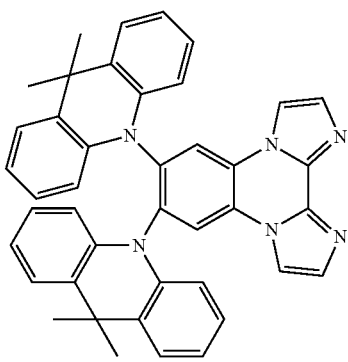

-continued
7
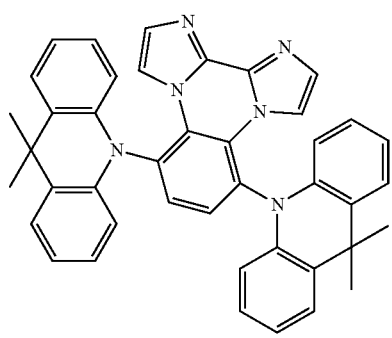
8
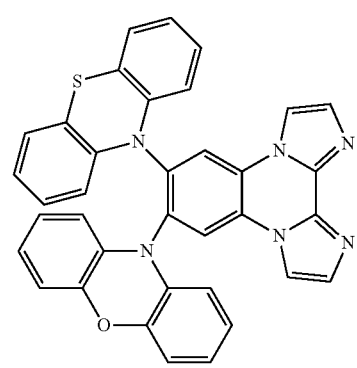
9
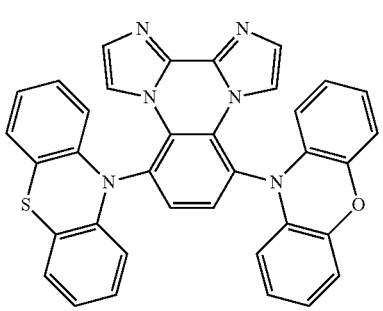
10
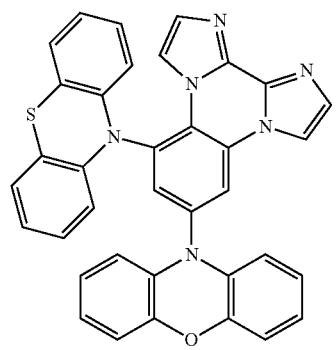
-continued
11
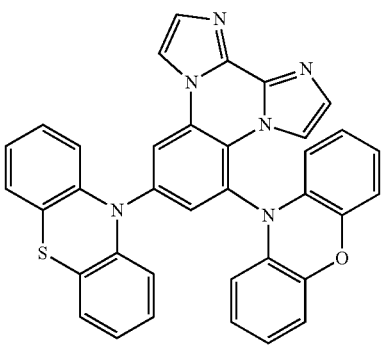
12
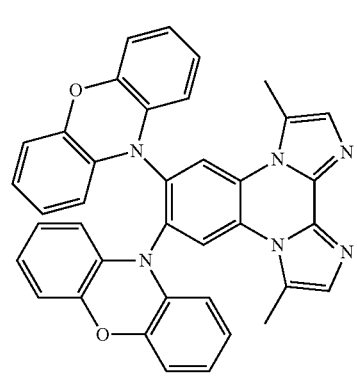
13
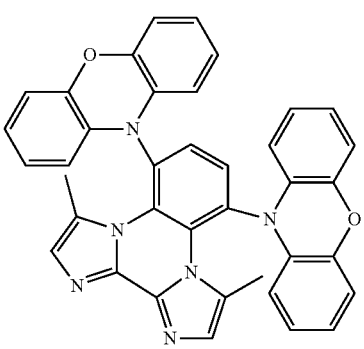
14
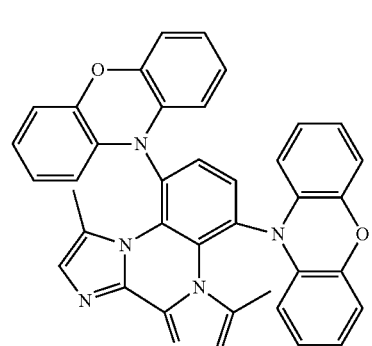

15
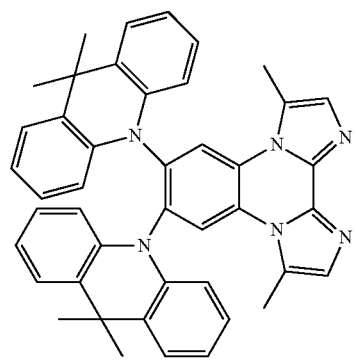
16
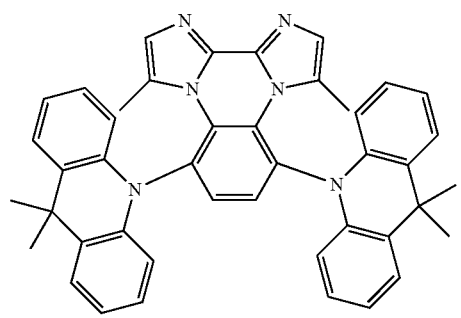
17
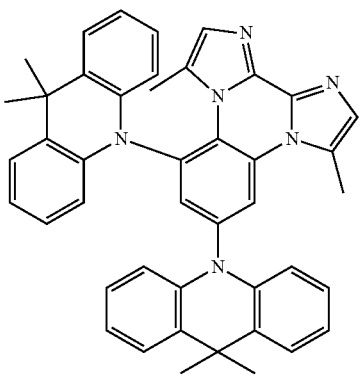
18
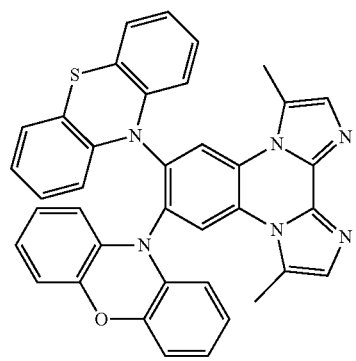
19
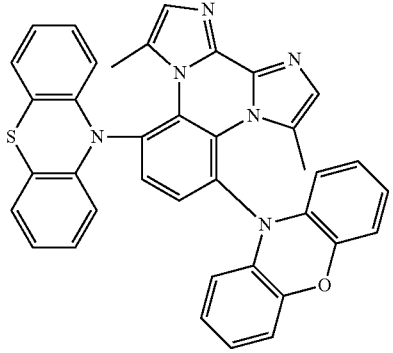
20
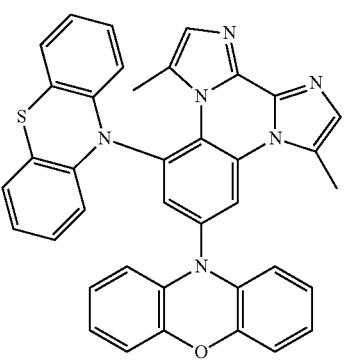
21
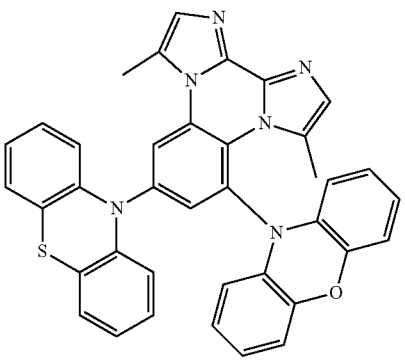
22
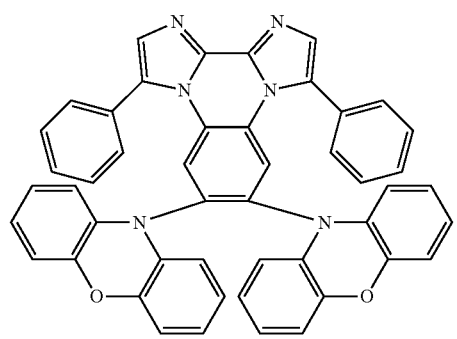

23
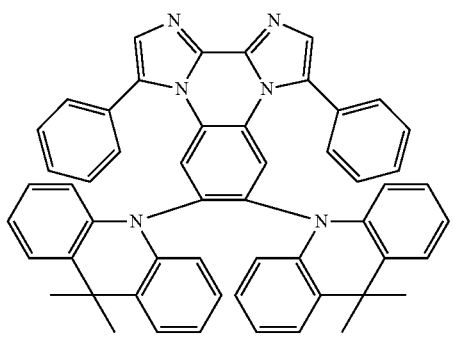
24
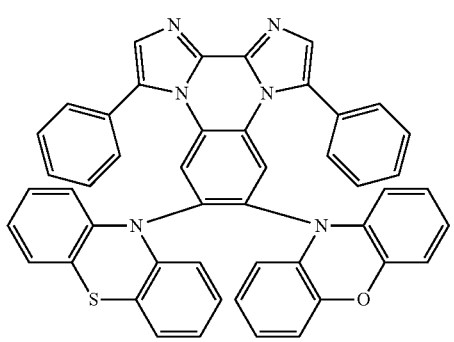
25
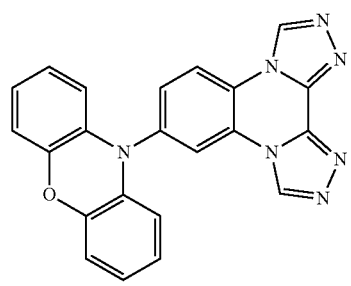
26
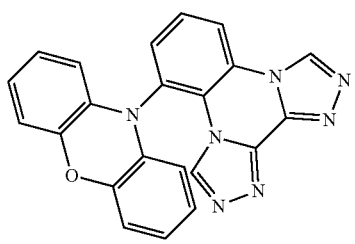
27
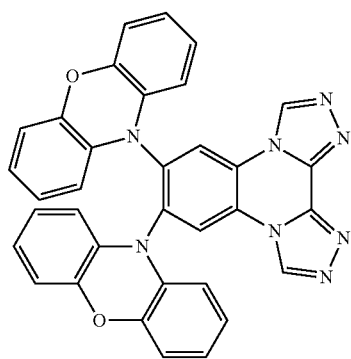
28
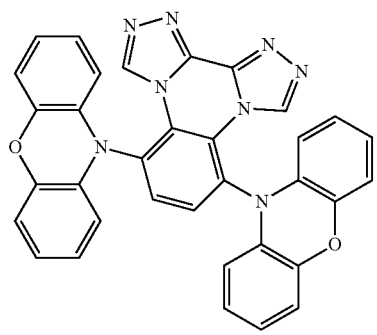
29
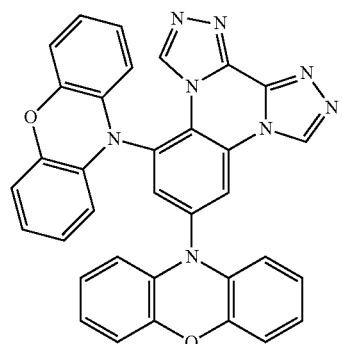
30
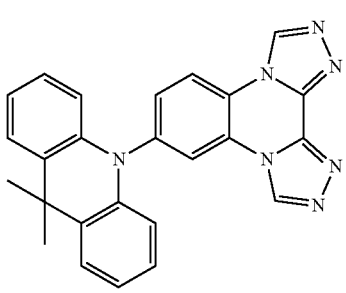
31
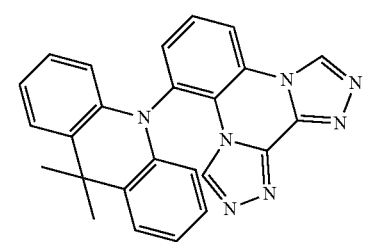
32
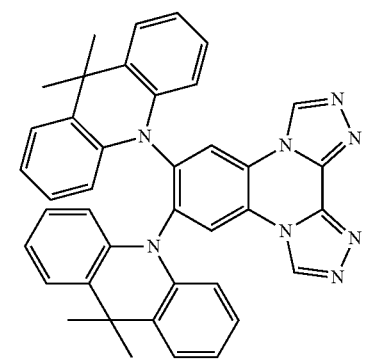

33
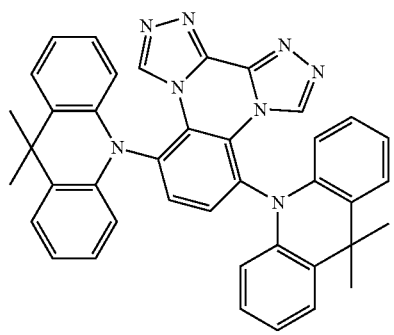
34
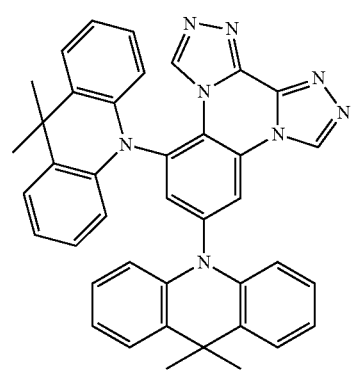
35
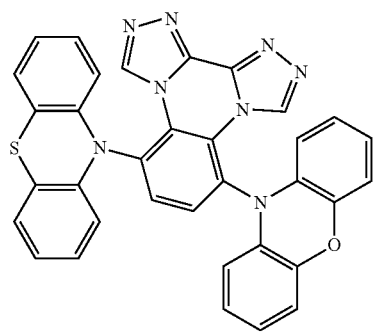
36
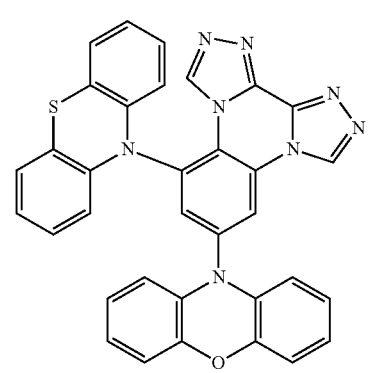
37
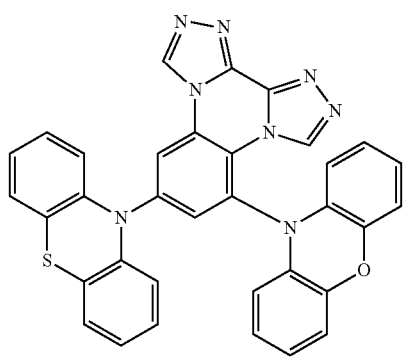
38
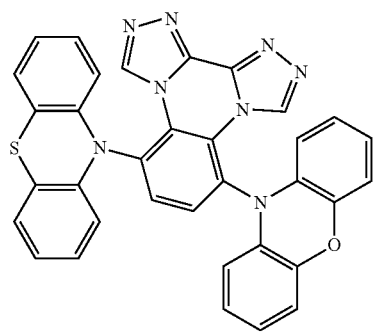
39
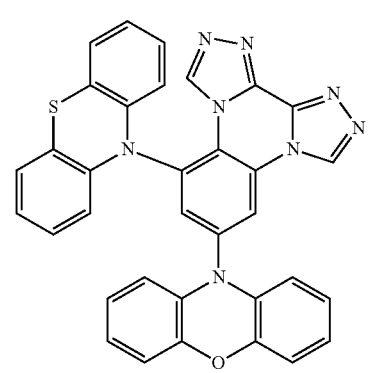
40
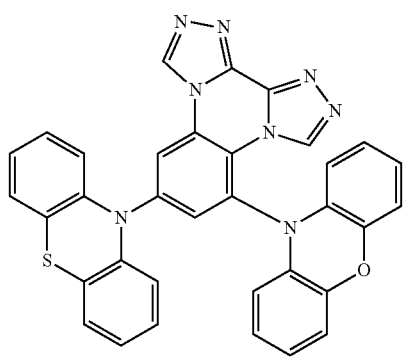
41
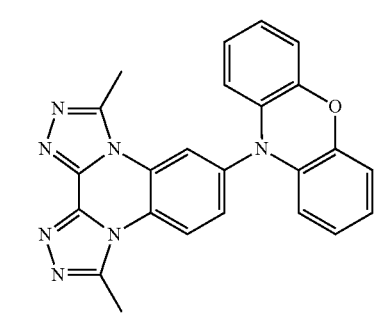
42
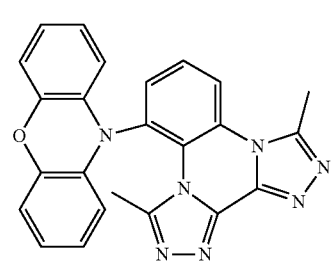

-continued

53
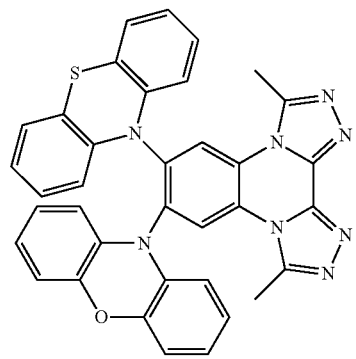
55
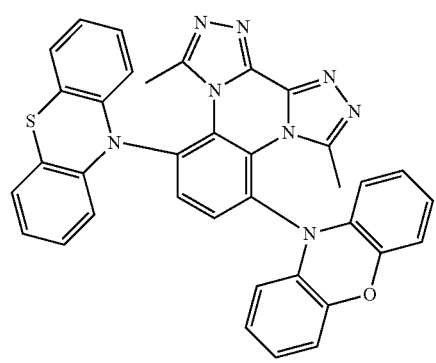
55
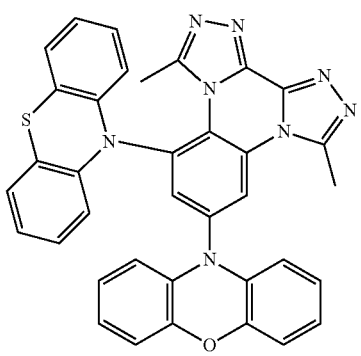
56
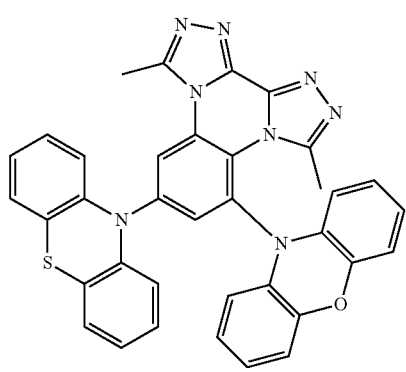
57
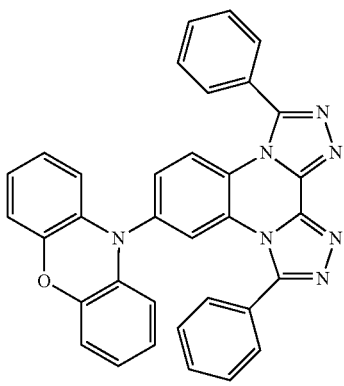
58
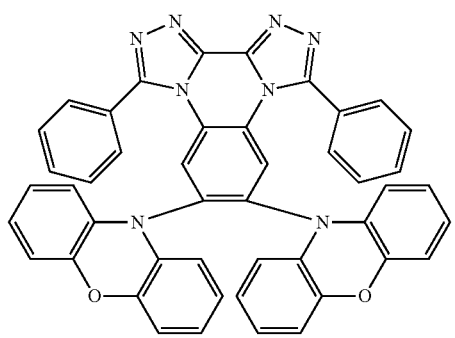
59
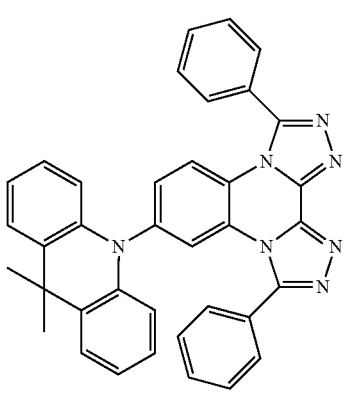
60
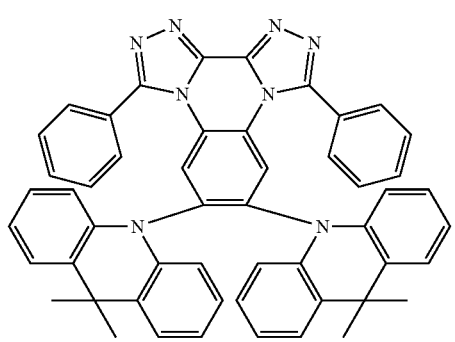

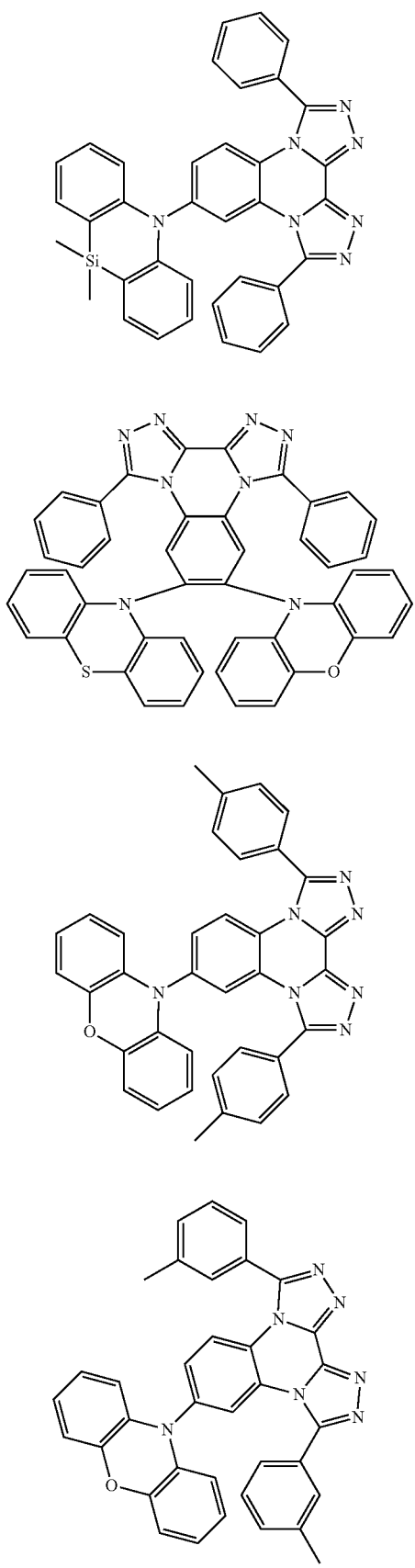

In one embodiment, the chemical bond having the curve

may refer to a broken bond. The broken bond may be able to connect with another broken bond to form a complete chemical bond. The broken bonds may cause two functional groups to connect according to a general formula. Further, the functional group having the broken bonds may directly connect to certain position of a phenyl group.

In one embodiment, the disclosed N-containing heterocyclic compounds have the thermally activated delayed fluorescence (TADF) property.

The disclosed nitrogen-containing heterocyclic compound may be synthesized by any appropriate methods. For illustrative purposes, the synthesis route and the synthesis method of

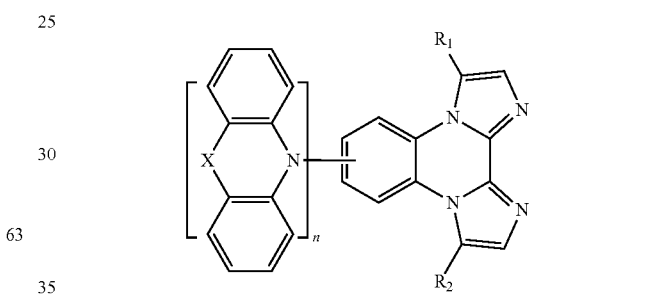

are described as an example.

The synthesis route is shown as below.

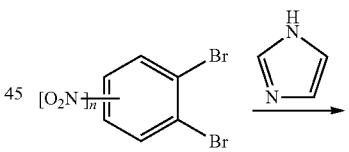

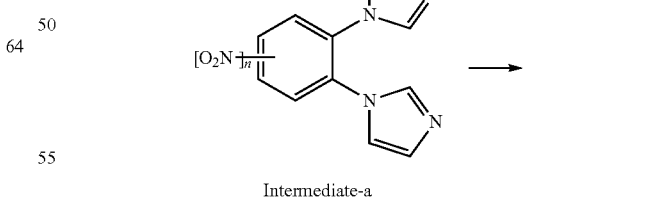

Intermediate-a

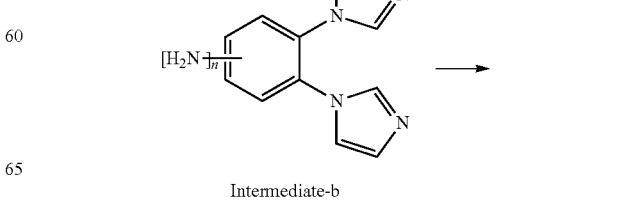

Intermediate-b

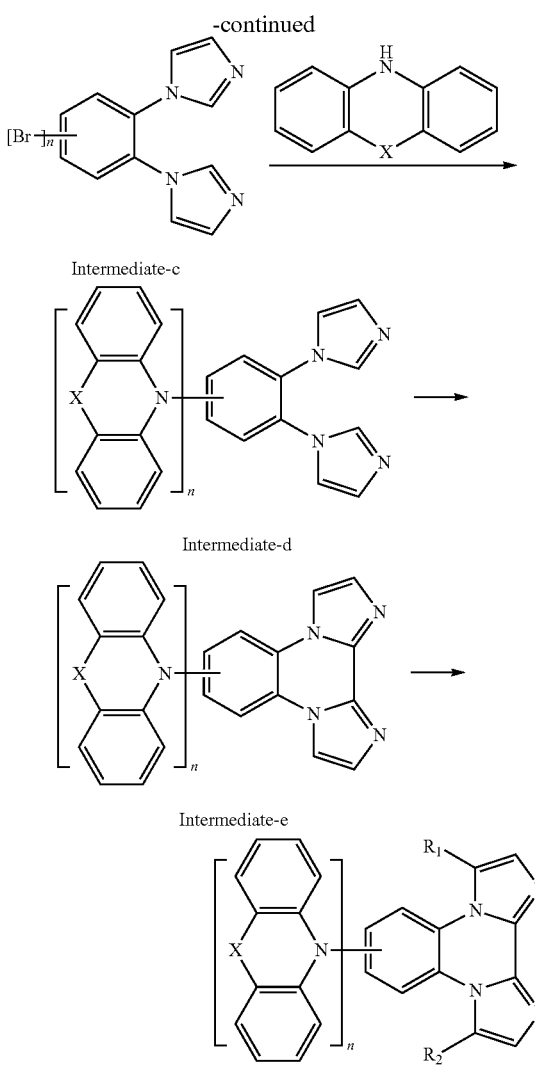

Intermediate-c

Intermediate-d

Intermediate-e

Where X, $R_1$, and $R_2$ may be the same as the previously described elements and chemical structures, or other appropriate elements and chemical structures. n may be an integer from 1 to 4.

The synthesis of the nitrogen-containing heterocyclic compound may include following steps. The precursors (1 eq.) my react with imidazole (2.5 eq.) in the environment having $K_2CO_3$ (2 eq.) and $Cu_2O$, etc. to form the intermediate-a. Then, the product(s) may have a reduction reaction with a hydrogen gas; and the intermediate-b may be obtained. The intermediate-b may have the amino group to be brominated under the effects of $NaNO_2$ (3 n eq.), HBr (2.5 n eq.), and CuBr (1.05 n eq.); and the intermediate-c may be obtained. Then, the intermediate-c (1 eq.) may have a Buchwald-Hartwig coupling reaction with

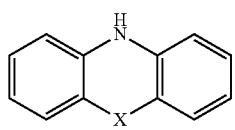

(1.1 n eq.) under the effect of $Pd(OAc)_2$ (0.05 n eq.), tri-tert-butylphosphine (0.075 n eq) and $Cs_2CO_3$ (1.5 n eq.); and the intermediate-d may be obtained. The intermediate-d (1 eq.) may react with n-butyllithium at a temperature of −78° C. Then, $I_2$ (1.1 eq.) may be added into the products. After a reaction under a heating condition, the intermediate-e may be obtained. The intermediate-e may react with the corresponding bromide (5 eq.) under the effect of $K_2CO_3$ (4 eq.), $PdCO_3$ (0.1 eq.) and triphenylphosphine (0.2 eq.); and the targeted compound may be obtained.

In certain other embodiments, such a synthesis method may be improved or modified to synthesize other compounds consistent with the disclosed embodiments. For example,

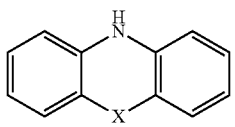

may be substituted or replaced by one or more of the compounds having the general formula (II). That is, a hydrogen atom may be connected to the broken bond. When

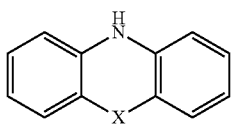

is substituted by two or more of the compounds having the general formula (II), the two or more compounds or the mixture may be simultaneously added to substitute bromide atoms by a one-step substitution, or a multiple-step substitution.

According to the disclosed embodiments, the disclosed nitrogen-containing heterocyclic compounds may be applied in organic photoelectric apparatus. The organic photoelectric apparatus may be OLED, photovoltaic devices, organic photoelectric sensors, and organic data storage devices, etc.

Further, according to the disclosed embodiments, an organic photoelectric apparatus is provided. The organic photoelectric apparatus may include an anode layer, a cathode layer, and at least one organic layer formed between the anode layer and the cathode layer. The organic layer may include one or more of the disclosed compounds.

In one embodiment, the organic layer may include a light-emitting layer. The light-emitting layer may include one or more of the disclosed compounds. The disclosed compound may be used as at least one of doping material, co-doping material, and host material, etc.

In one embodiment, the organic layer may also include one or more of a hole-transport layer, a hole injection layer, an electron barrier layer, a hole barrier layer, an electron transport layer, and an electron injection layer, etc.

Definitions

The technical and scientific terms used herein, if not specified, may include ordinary meaning of the terms as known to one of ordinary skill in the art. The terms defined herein may be interpreted according to the present disclosure.

As used herein, unless otherwise specified, the term "alkyl group" refers to completely saturated hydrocarbon (without double bond or triple bond). The alkyl group may be linear alky group or branched alkyl group. The alky group may have 1-30 carbon atoms, 1-20 carbon atoms, 1-10 carbon atoms, and 1-6 carbon atoms, etc. For example, the range 1-30 may include all the integers between 1 and 30 and including 1 and 30, i.e., including 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. For example, the alky group may be selected from methyl group, ethyl group, propyl group, isopropyl group, n-butyl group, isobutyl group, sec-butyl group, tertbutyl group, pentyl group, and hexyl group, etc. The alkyl group may be substituted alkyl group, or non-substituted alkyl group.

As used herein, unless otherwise specified, the term "aromatic group" refers to carbon ring(s) having completely localized π-electrons throughout all the rings. The aromatic group may include monocyclic aromatic group or polycyclic aromatic group. The polycyclic aromatic group may be a system having two or more aromatic rings such as two or more benzene rings. The two or more aromatic rings may be bonded by single bond, or condensed by shared chemical bonds. The number of carbon atoms in the aromatic group may vary. For example, the aromatic group may have 6-30 carbon atoms. The range 6-30 may include all the integers between 6 and 30 and including 6 and 30, i.e., including 6, 7, 8, 9, 10, 11, 12, 13, 14, 15, 16, 17, 18, 19, 20, 21, 22, 23, 24, 25, 26, 27, 28, 29, and 30. The exemplary aromatic group may include, but be not limited to, benzene group, biphenyl group, nathpho group, anthryl group, phenanthryl group and pyrenyl group, etc. The aromatic group may be substituted aromatic group or non-substituted aromatic group.

As used herein, unless otherwise specified, the term "heterocyclic aromatic group" refers to a monocyclic or polycyclic aromatic group, having one or more hetero atoms. The hetero atoms may be any element other than carbon. For example, the hetero atoms may include N, O and S, etc. The number of carbon atoms in the heterocyclic aromatic group may vary. For example, the heterocyclic aromatic group may have 1-20 carbon atoms. The range 1-20 may include all the integers between 1 and 20, and including 1 and 20, i.e., including 1, 2, 3, 4, 5, 6, 7, 8, 9, 10, 11, 12, 13, 14, 15, 16, 17, 18, 19 and 20. Further, the heterocyclic aromatic group may have 1-30 ring skeleton atoms. The range 1-30 may include all the integers between 1 and 30 and including 1-30, i.e., including 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30. Further, the term "heterocyclic aromatic group" may include a fused-ring system. In this system, two rings (e.g., at least one aromatic ring and at least one heterocyclic aromatic ring or at least two heterocyclic aromatic rings) may share at least one chemical bond. The exemplary heterocyclic aromatic group may include, but be not limited to, furyl group, furazanyl group, thienyl group, benzothiophenyl group, thalazinyl group, pyrrolyl group, oxazolyl group, benzoxazolyl group, 1,2,3-oxadiazolyl group, 1,2,4-oxadiazolyl group, thiazolyl group, 1,2,3-thiadiazolyl group, 1,2,4-thiadiazolyl group, benzothiazolyl group, imidazolyl group, benzimidazolyl group, indyl group, indazolyl group, pyrazol group, benzopyrazol group, isoxazolyl group, benzisoxazolyl group, isothiazol group, triazolyl group, benzotriazol group, thiadiazolyl group, tetrozolyl group, pyridyl group, pyridazinyl group, pyrimidinyl group, pyrazinyl group, purinyl group, pteridinyl group, quinolyl group, isoquinolyl group, quinazolinyl group, quinoxalinyl group, cinnolinyl group and triazinyl group, etc. The heterocyclic aromatic group may be substituted heterocyclic aromatic group or non-substituted heterocyclic aromatic group.

Organic Photoelectric Apparatus

The disclosed organic photoelectric apparatus may include organic light-emitting diode (OLED), organic solar cell, organic photoelectric sensor and organic data storage apparatus, etc.

An OLED may include an anode, a cathode and one or more organic layers between the anode and the cathode. The one or more organic layers may include at least one light-emitting layer; and the light-emitting layer may include the disclosed compound. The OLED may also include a hole transport layer (HTL), a hole injection layer (HIL), an electron barrier layer (EBL), a hole barrier layer (HBL), an electron transport layer (ETL), an electron injection layer (EIL) and a combination thereof. One or more of such layers may include the disclosed compound. The disclosed compound may be used as one or more of doping material, co-doping material and host material of the light-emitting layer. The light-emitting layer may include two or more disclosed compounds.

When the light-emitting layer includes two materials, the mass percentile of the first material may be in a range of approximately 0%-50% but not include 0. The first material may be used to emit light after being electrically activated. Thus, the first material may be referred to as a doping material. The mass percentile of the second material may be in a range of 100%-50% but not include 100%. Holes from the anode and electrons from the cathode may recombine to generate excitons in the second material; and the excitons may be transported to the doping material by the second material. Thus, the second material may be referred to as a host material.

When the light-emitting layer include the first material and the second material, the mass percentile of the first material and the second material may all be in a range of 0%-50% but not include 0. The first material may emit light after being activated; and may be referred to as a doping material. The other one or more material may be used to transport the exciton energy to the doping material; and may be referred to as a co-doping material. Except such materials, the remaining one or more materials may have a mass percentile or a total mass percentile in a range of approximately 100%-50% but not include 100%. Such remaining one or more materials may be used to transport excitons generated by the recombination of the electrons from the cathode and the holes from the anode to the doping material and the co-doping material; and may be referred as to a host material. The mass percentiles of the doping material, the co-doping material and the host material may be any other appropriate values.

For illustrative purposes, OLED structures are described as examples of the organic photoelectric apparatus utilizing the disclosed compounds. FIGS. 1-5 illustrate exemplary OLED structures consistent with the disclosed embodiments.

As shown in FIGS. 1-5, the OLED utilizing the disclosed compounds may include a substrate layer 100, and an anode layer 110 formed over the substrate layer 100. The anode layer 110 and the substrate layer 100 may be referred as an anode substrate. The OLED may also include at least a light-emitting layer 130 formed over the anode layer 110, and a cathode layer 120 formed over the light-emitting layer 130. That is, the light-emitting layer 130 may be in between the anode layer 110 and the cathode layer 120.

Figure 2:
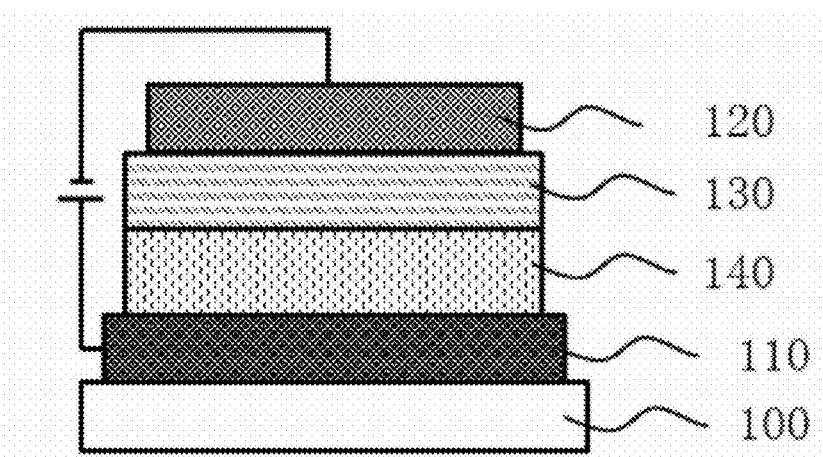
FIG. 2 illustrates another exemplary OLED consistent with the disclosed embodiments.

In one embodiment, as shown in FIG. 1, the anode layer 110 and the cathode layer 120 of the OLED may only have the light-emitting layer 130 in there-between. The electrons and holes may recombine to activate the light-emitting layer 130 to emit light. The light-emitting layer 130 may be made of one or more of the disclosed compounds In certain other embodiments, as shown in FIG. 2, a hole transport layer (HTL) 140 may be formed between the light-emitting layer 130 and the anode layer 110. That is, the HTL 140 and the light-emitting layer 130 are in between the anode layer 110 and the cathode layer 120 of the OLED. The HTL 140 may transport the holes to the light-emitting layer 130. At least one of the light-emitting layer 130 and the HTL 140 may be made of one or more of the disclosed compounds.

Figure 3:
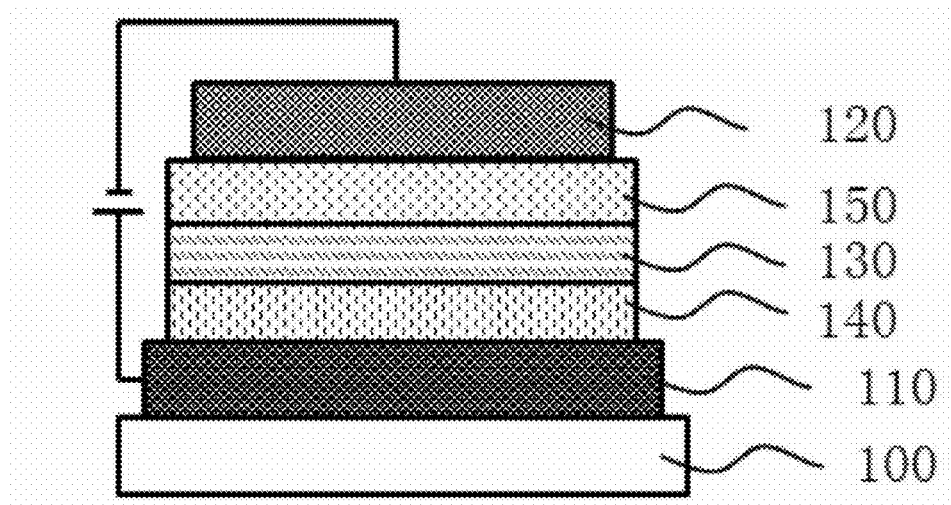
FIG. 3 illustrates another exemplary OLED consistent with the disclosed embodiments.

In still certain other embodiments, as shown in FIG. 3, an electron transport layer (ETL) 150 may be formed between the cathode layer 120 and the light-emitting layer 130. That is, the HTL 140, the light-emitting layer 130 and the ETL 150 may be in between the anode layer 120 and the cathode layer 110. The ETL 150 may transport electrons to the light-emitting layer 130. At least one of the HTL 140, the light-emitting layer 130 and the ETL 150 may be made of one or more of the disclosed compounds.

Figure 4:
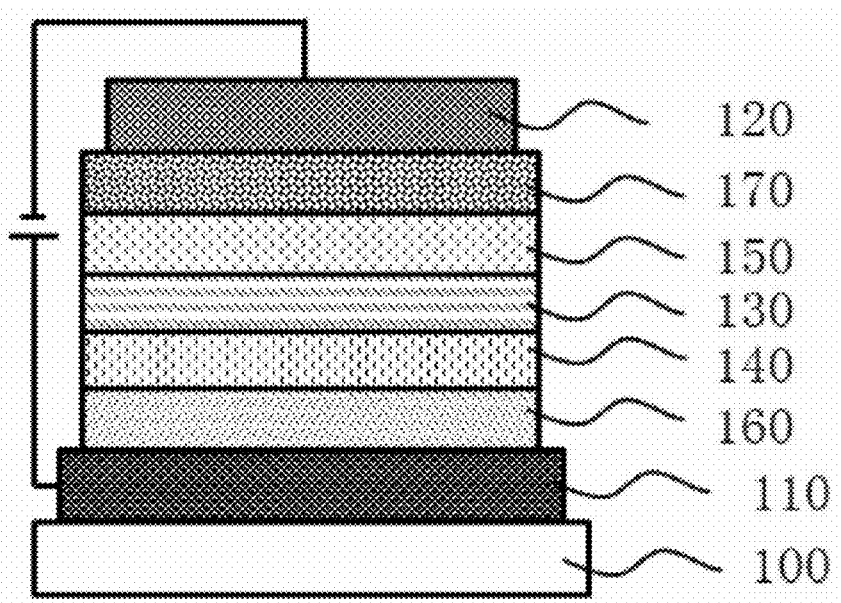
FIG. 4 illustrates another exemplary OLED consistent with the disclosed embodiments.

In still certain other embodiments, as shown in FIG. 4, a hole injection layer (HIL) 160 may be formed between the anode layer 110 and the HTL 140; and an electron injection layer (EIL) 170 may be formed between the cathode layer 120 and the ETL 150. That is, the HIL 160, the HTL 140, the light-emitting layer 130, the ETL 150 and the ETL 170 may be in between the anode layer 110 and the cathode layer 120. The HIL 160 may be able to improve the ability to transport the holes from the anode layer 110 to the light-emitting layer 130. The EIL 170 may be able to improve the ability to transport the electrons from the cathode layer 120 to the light-emitting layer 130. Accordingly, the drive voltage of the OLED may be reduced. At least one of the HIL 160, the HTL 140, the light-emitting layer 130, the ETL 150 and the ETL 170 may be made of one or more of the disclosed compounds.

Figure 5:
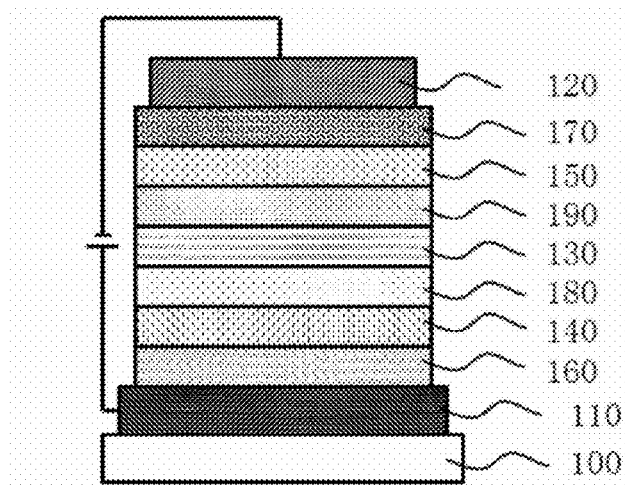
FIG. 5 illustrates another exemplary OLED consistent with the disclosed embodiments.

In still certain other embodiments, as shown in FIG. 5, an electron barrier layer (EBL) 180 may be formed between the light-emitting layer 130 and the HTL 140; and a hole barrier layer (HBL) 190 may be formed between the light-emitting layer 130 and the ETL 150. That is, the HIL 160, the HTL 140, the EBL 180, the light-emitting layer 130, the HBL 190, the ETL 150 and the ETL 170 may be in between the anode layer 110 and the cathode layer 120. The EBL 180 may be able to prevent electrons from entering into the HTL 140 from the light-emitting layer 130; and the HBL 190 may be able to prevent the holes from entering into the ETL 150 from the light-emitting layer 130. At least one of the HIL 160, the HTL 140, the EBL 180, the light-emitting layer 130, the HBL 190, the ETL 150 and the ETL 170 may be made of one or more of the disclosed compounds.

The anode layer 110 may be made of any appropriate material with a relatively large work function. The material used for the anode layer 110 may include Cu, Au, Ag, Fe, Cr, Ni, Mn, Pd, Pt, or a combination thereof. The material used for the anode layer 110 may also include a metal alloy of Cu, Au, Ag, Fe, Cr, Ni, Mn, Pd, and Pt, etc. Further, the material used for the anode layer 110 may also be metal oxide, such as SnO, ZnO, ITO, IZO, or a combination thereof. Further, the material used for the anode layer 110 may also be a conductive polymer, such as polyaniline, polypyrrole, poly (3-methylthiophene), or a combination thereof. In one embodiment, the anode layer 110 is made of ITO.

The cathode layer 120 may be made of any appropriate material with a relatively small work function, such as Al, Mg, Ag, In, Sn, Ti, Ca, Na, K, Li, Yb, Pb, or a combination thereof. The cathode layer 120 may also be made of a multiple-layer material, such as LiF/Al, or Liq(8-quinolinol)/Al, etc. In one embodiment, an alloy of Mg and Ag or a double layer structure of LiF/Al may be used as the material of the cathode layer 120.

The HIL 160 may be made of any appropriate material such that the injection of holes from the anode layer 110 to the organic interface layer may be increased, and the HIL 160 may have a desired adhesion to the surface of the ITO anode 110. The material used for the HTL 160 may include the polymers with the HOMO energy level matching the work function of ITO, such as porphyrin compounds of CuPc, naphthylenediamine-containing stellate triphenylamine derivatives of 4,4',4"-tris[2-naphthyl-phenyl-amino]triphenylamine (TNATA) and poly(3,4-Ethylenedioxythiophene): polystyrene sulfonate (PEDOT:PSS), and electron withdrawing nitrogen-containing heterocyclic compounds of hexaazatriphenylenehexacabonitrile (HATCN), etc.

The HTL 140 and the EBL 180 may be made of any appropriate material having a relatively high glass transition temperature and a relatively high hole mobility. The material used for the HTL 140 and the EBL 180 may include the diphenyl diamine derivatives of N,N'-Di-[(1-naphthalenyl)-N,N'-diphenyl]-1,1'-biphenyl)-4,4'-diamine (NPD), the crossing diphenyl diamine derivatives of 2',7,7'-tetrakis(N,N-diphenylamino)-9,9-spirobifluorene (spiro-TAD), and the stellate triphenylamine derivatives of 4,4',4"-Tris(carbazol-9-yl)triphenylamine (TCTA), etc.

The HBL 190 and the ETL 150 may be made any appropriate material having a relatively low HOMO energy level, and a relatively high electron mobility. The material used for the HBL 190 and ETL 150 may include the metal-quinolinolato complexes of bis(2-methyl-8-quinolinolato-N1,O8)-(1,1'-Biphenyl-4-olato)aluminum (BAlq), tris(8-hydroxyquinolinato)aluminum (Alq), 8-hydroxyquinoline lithium, the phenanthroline derivatives of 4,7-diphenyl-1,10-phenanthroline (BPhen), the imidazoline derivatives of 1,3,5-Tris(1-phenyl-1H-benzimidazol-2-yl)benzene (TPBI), or the triazine derivatives of 2,4,6-Tri(9H-carbazol-9-yl)-1,3,5-triazine, etc.

The OLED having the disclosed compounds may be formed by any appropriate methods. In one embodiment, the method for forming the OLED may include forming an anode layer on a smooth transparent or opaque substrate; forming an organic layer made of at least one of the disclosed compounds on the anode layer; and forming a cathode layer on the organic layer. The organic layer may be formed by any appropriate process, such as a thermal evaporation process, a sputtering process, a spin-coating process, a dip-coating process, or an ion deposition process, etc.

The following embodiments will further describe the advantages of the disclosed compounds and OLEDs having the disclosed compounds. Exemplary embodiments 1-12 describe the simulation process of exemplary compounds consistent with the disclosed embodiments.

The energy level difference of the minimum singlet state ($S_1$) and the minimum triplet state ($T_1$) of an organic material may be simulated by Guassian 09 software (Guassian Inc.). The detailed simulation method of the energy level difference $\Delta E_{st}$ may refer to J. Chem. Theory Comput., 2013, DOI: 10.1021/ct400415r. The optimization of the molecular structure and the activation may all be obtained by TD-DFT method "B3LYP" and base group "6-31g(d)".

In embodiment 1, a simulation process is performed on the compound 1.

In embodiment 2, a simulation process is performed on the compound 5.

In embodiment 3, a simulation process is performed on the compound 12.

In embodiment 4, a simulation process is performed on the compound 18.

In embodiment 5, a simulation process is performed on the compound 22.

In embodiment 6, a simulation process is performed on the compound 25.

In embodiment 7, a simulation process is performed on the compound 30.

In embodiment 8, a simulation process is performed on the compound 36.

In embodiment 9, a simulation process is performed on the compound 44.

In embodiment 10, a simulation process is performed on the compound 51.

In embodiment 11, a simulation process is performed on the compound 57.

In embodiment 12, a simulation process is performed on the compound 63.

The simulation results are illustrated in Table 1.

TABLE 1

|  | Compound | $S_1(eV)$ | $T_1(eV)$ | $\Delta E_{st}(eV)$ |
| --- | --- | --- | --- | --- |
| Embodiment 1 | 1 | 3.04 | 2.78 | 0.26 |
| Embodiment 2 | 5 | 2.85 | 2.70 | 0.15 |
| Embodiment 3 | 12 | 2.98 | 2.76 | 0.22 |
| Embodiment 4 | 18 | 2.90 | 2.73 | 0.17 |
| Embodiment 5 | 22 | 2.84 | 2.56 | 0.28 |
| Embodiment 6 | 25 | 2.82 | 2.71 | 0.11 |
| Embodiment 7 | 30 | 3.23 | 3.19 | 0.05 |
| Embodiment 8 | 36 | 3.32 | 3.15 | 0.18 |
| Embodiment 9 | 44 | 2.86 | 2.84 | 0.01 |
| Embodiment 10 | 51 | 3.36 | 3.09 | 0.27 |
| Embodiment 11 | 57 | 2.86 | 2.70 | 0.16 |
| Embodiment 12 | 63 | 2.90 | 2.69 | 0.21 |

As shown in Table 1, the energy level difference $\Delta E_{st}$ between the minimum singlet state $S_1$ and the triplet stage $T_1$ may all be relatively small, from the embodiment 1 to the embodiment 12. Thus, the compounds in Table 1 may all be able to achieve a reverse intersystem crossing; and may have the performances of the TADF materials.

Exemplary embodiments 13-18 describe exemplary synthesis routes and processes of the disclosed compounds consistent with the disclosed embodiments.

Embodiment 13 describes the synthesis route and synthesis process of the compound 1. The first step of the synthesis process of the compound 1 may be to synthesize the intermediate 1-a.

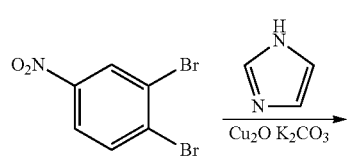

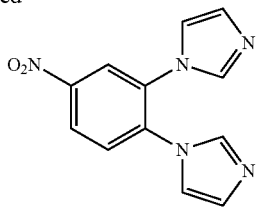

1-a

Specifically, under the environment of Ar, 1,1-dibromo-4-nitrophenyl (2.8 g, 10 mmol), Imidazole (1.7 g, 25 mmol), $K_2CO_3$ (2.7 g, 20.0 mmol) and $Cu_2O$ (7.2 mg, 0.05 mmol) may be put into a reaction flask; and 20 ml DMSO may be added as a solvent. The mixture may be stirred; and may react for 2 days at 150° C. The reaction product may be cooled down to the room temperature; and may be filtered using diatomite. Then, DI water may be added into the organic phase; and dichloromethane may be used to extract the organic phase. The obtained organic phase may be dried by dehydrated $MgSO_4$, and purified by a silicone gel chromatographic column. Thus, the intermediate 1-a (1.8 g, yield 71%) may be obtained.

The second step of the synthesis process of the compound 1 may be to synthesize the intermediate 1-b illustrated in the follow synthesis route.

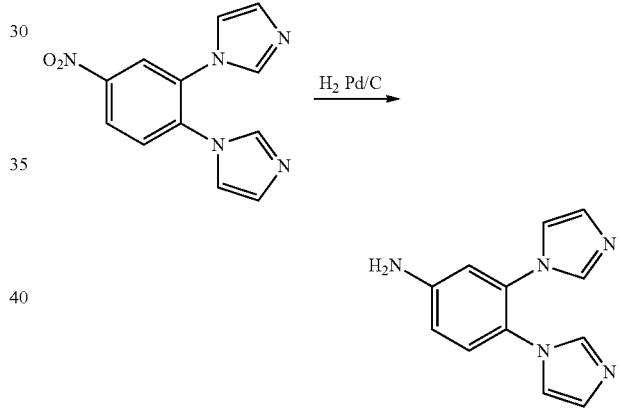

1-b

The intermediate 1-a (1.8 g, 7.1 mmol) may be dissolved in methanol. Under the protection of Ar gas, 1 g Pd/C may be slowly added into the solution. After substituting the gas in the reaction flask with hydrogen, the reaction may be continued for 20 hours in the hydrogen environment. After filtering and evaporating the solvent, the intermediate 1-b (1.2 g, 55%) may be obtained.

The third step of the synthesis process of the compound 1 may be to synthesize the intermediate 1-c illustrated in the following synthesis route.

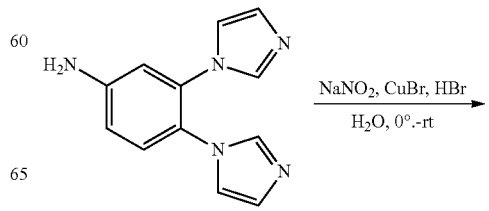

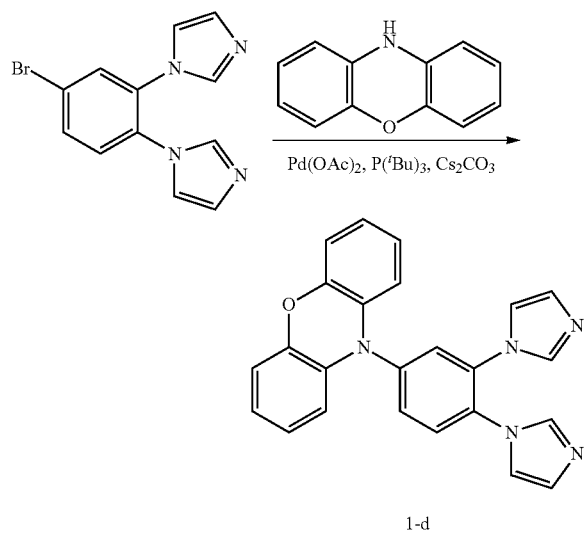

1-c

NaNO$_2$ (1.1 g, 15.9 mmol) may be dissolved in 2 ml water. Such a solution may be slowly added into a mixture of the intermediate 1-b (1.2 g, 5.3 mmol) and 2.9 ml of HBr (approximately 15.0 mmol) with a concentration of 48%; and stirred for 1 hour (0° C.). Under the ice bath condition (0° C.), 2 ml CuBr in HBr solution (0.8 g, 5.6 mmol) may be added into the mixture; the reaction may continue for 1 hour in the ice bath. Then, the mixture may be heated to 60° C. to react for 2 hours. After being cooling down, an extraction process may be performed using 50 ml ethyl acetate. The organic layer may be washed by water for a couple of times; and dried by dehydrated MgSO$_4$. After filtering and evaporating the solvent, the intermediate 1-c (1.0 g, yield 65%) may be obtained.

The fourth step of the synthesis process of the compound 1 may be to synthesize the intermediate 1-d illustrated in the following synthesis route.

1-d

Under an Ar environment, the intermediate 1-c (1.0 g, 3.5 mmol), phenoxazine (0.7 g, 3.9 mmol), Pd(OAc)$_2$ (44.9 mg, 0.2 mmol), tri-tert-butylphosphine (60.7 mg, 0.3 mmol) and Cs$_2$CO$_3$ may be dissolved in Toluene. The mixture may be refluxed for 12 hours. Then, the solvent may be evaporated under vacuum. Then, the product may be added into pentane; and stirred. After a filtering process, the product may be purified by a silicone gel chromatographic column; and the intermediate 1-d (0.7 g, yield 51%) may be obtained.

The fifth step of the synthesis process of the compound 1 may be to synthesize the final compound 1 illustrated in the following synthesis route.

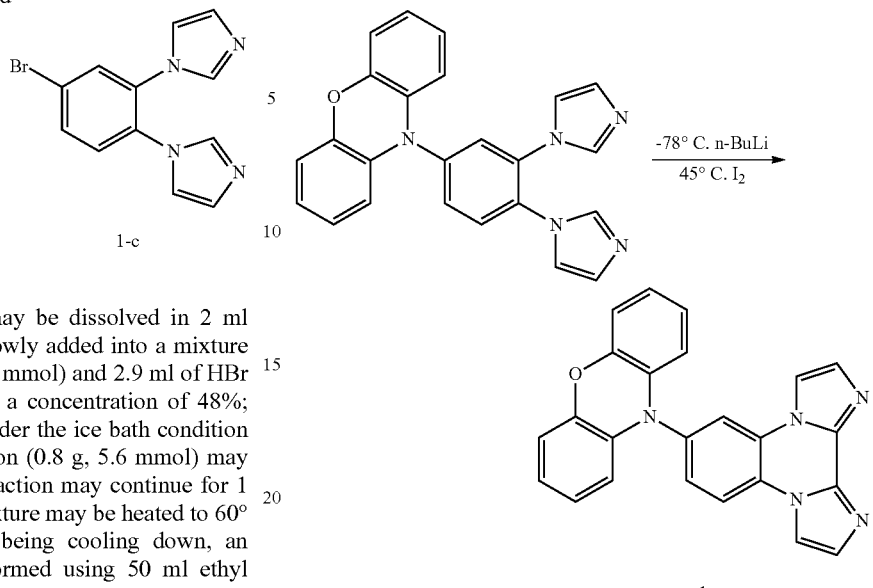

1

In a liquid nitrogen-acetone bath (−78° C.), the hexane solution of n-Buli (2.7 ml, 4.3 mmol) may be slowly dropped into a dehydrated THF solution of the intermediate 1-d (0.7 g, 1.8 mmol); and the mixture may be stirred for 1 hour at −78° C. Then, the mixture may be slowly heated to 45° C.; and added into the dehydrated THF solution of I$_2$ (0.5 g, 2.5 mmol). The reaction may be continued for 1 day. Then, a saturated NaCl solution may be added; and dichloromethane may be used to extract the organic phase. After being dried by dehydrated MgSO$_4$, the product may be purified by a silicone gel chromatographic column; and the compound 1 (0.36 g, yield 52%) may be obtained.

An LC-MS method may be used to analyze the final product (the obtained compound 1). The ESI-MS (m/z) of the final product is approximately 390.1 [M+H]$^+$. Such a value corresponds to the molecular weight of the compound 1.

Embodiment 14 describes the synthesis route and the synthesis process of the compound 5. The starting precursor may be 1,2-dibromo-3,5-dinitro-benzene (3.2 g, 10 mmol) instead of 1,1-dibromo-4-nitrophenyl in the embodiment 13. The corresponding equivalents may be changed. Other precursors and process conditions may be similar to those of the embodiment 13 (compound 1). After the synthesis process, the compound 5 (0.4 g, yield 7%) may be obtained.

An LC-MS method may be used to analyze the final product (the obtained compound 5). The ESI-MS (m/z) of the final product is approximately 571.1 [M+H]$^+$. Such a value corresponds to the molecular weight of the compound 5.

Embodiment 15 describes the synthesis route and synthesis process of the compound 22. The first step of the synthesis process of the compound 22 may be to synthesize the intermediate 22-a. The starting precursor may be 1,2-dibromo-4,5-dinitro-benzene (3.2 g, 10 mmol) instead of 1,1-dibromo-4-nitrophenyl. The corresponding equivalents may be changed. Other precursors and process conditions may be similar to those of the embodiment 13 (compound 1). After the synthesis process, the intermediate 22-a (0.3 g, yield 5%) illustrated in the following synthesis route may be obtained.

The second step of the synthesis process of the compound 22 may be to synthesize the final compound 22.

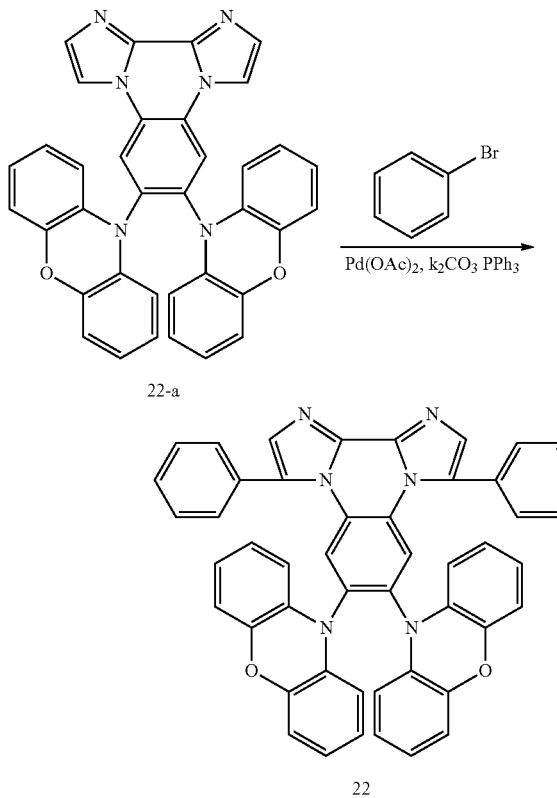

Specifically, under an environment of Ar, the intermediate 22-a (0.3 g, 0.53 mmol), bromobenzene (0.42 g, 2.65 mmol), Pd(OAc)$_2$ (11.2 mg, 0.05 mmol), PPh$_3$ (28.9 mg, 0.11 mmol) and dehydrated K$_2$CO$_3$ (0.29 g, 0.05 mmol) may be added into a reaction flask. DMF may be used as a solvent. The reaction may continue for 2 days at 150° C. After the reaction, the obtained product (s) may be cooled down to the room temperature; and may be filtered to obtain the organic phase using diatomite. Then, a saturated NaCl solution may be added into the organic phase; and dichloromethane may be used to perform an extraction process. The obtained organic phase may be concentrated, and purified by a silicone gel chromatographic column. Thus, the compound 22 (0.16 g, yield 43%) may be obtained.

An LC-MS method may be used to analyze the final product (the obtained compound 22). The ESI-MS (m/z) of the final product is approximately 723.1 [M+H]$^+$. Such a value corresponds to the molecular weight of the compound 22.

Embodiment 16 describes the synthesis route and synthesis process of the compound 30. The first step of the synthesis process of the compound 30 may be to synthesize the intermediate 30-a.

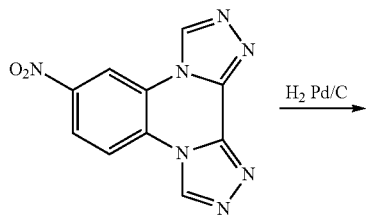

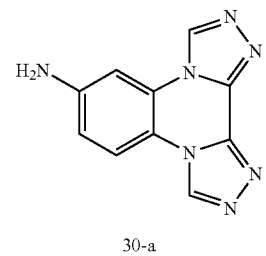

Specifically, under an environment of Ar, hexanitro-1,2, 4-triazole-imidazo-[4,3-a:3',4'-c]-quinoxaline (2.6 g, 10.2 mmol) may be dissolved in methanol; and 2 g Pd/C may be slowly added into the mixture. After substituting the gas in the reaction flask with hydrogen, the reaction may continue for 20 hours under the hydrogen environment. After filtering the product(s), and evaporating the solvent, the intermediate 30-a (1.6 g, yield 71%) may be obtained.

The second step of the synthesis process of the compound 30 may be to synthesize intermediated 30-b illustrated in the following synthesis route.

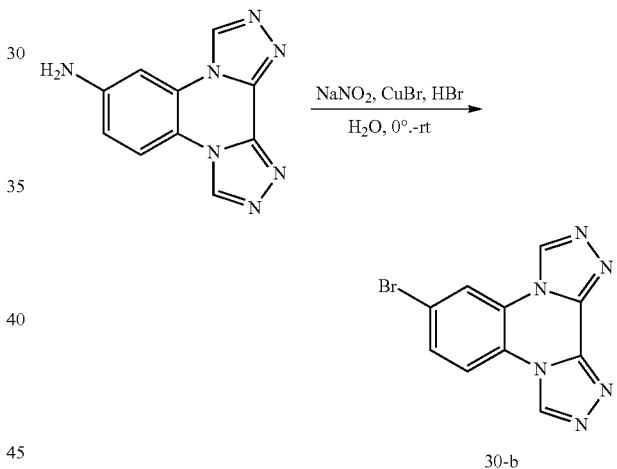

NaNO$_2$ (1.5 g, 21.6 mmol) may be dissolved in 4 ml water. Such a solution may be slowly added into a mixture of the intermediate 30-a (1.6 g, 7.2 mmol) and 2.4 ml of HBr (approximately 18.0 mmol) with a concentration of 48%; and stirred for 1 hour (0° C.). Under an ice bath condition (0° C.), 4 ml CuBr in HBr solution (1.1 g, 7.6 mmol) may be added into the mixture; and the reaction may continue for 1 hour in the ice bath. Then, the mixture may be heated to 60° C. to react for 2 hours. After being cooling down, an extraction process may be performed using 50 ml ethyl acetate. The organic layer may be washed by water for a couple of times; and dried by dehydrated MgSO$_4$. After filtering and evaporating the solvent, the intermediate 30-b (1.2 g, yield 59%) may be obtained.

The third step of the synthesis process of the compound 30 may be to synthesize the final compound 30 illustrated in the following synthesis route.

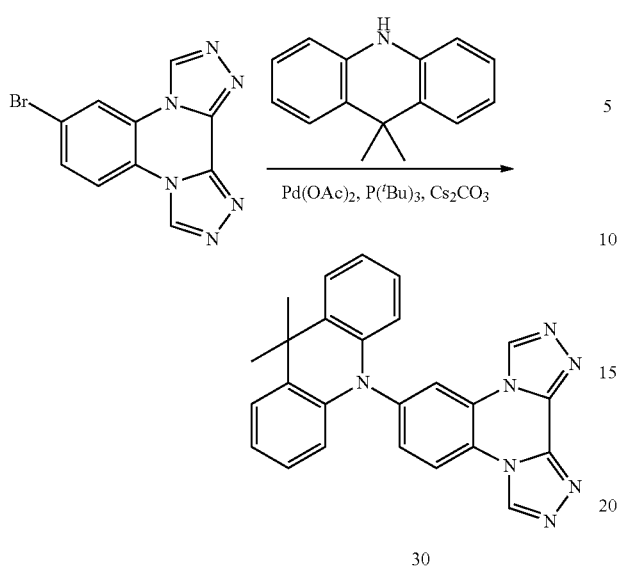

Under an Ar environment, the intermediate 30-b (1.2 g, 4.2 mmol), 9,9-dimethylcarbazine (0.96 g, 4.6 mmol), Pd(OAc)$_2$ (47.1 mg, 0.21 mmol), tri-tert-butylphosphine (63.7 mg, 0.32 mmol) and Cs$_2$CO$_3$ may be dissolved in Toluene; and the mixture may be refluxed for 8 hours. Then, the solvent may be evaporated under vacuum. Then, the product may be added into pentane; and stirred. After a filtering process, the product may be purified by a silicone gel chromatographic column; and the solid compound 30 (0.75 g, yield 43%) may be obtained.

An LC-MS method may be used to analyze the final product (the obtained compound 30). The ESI-MS (m/z) of the final product is approximately 418.1 [M+H]$^+$. Such a value corresponds to the molecular weight of the compound 30.

Embodiment 17 describes the synthesis route and the synthesis process of the compound 25. The synthesis route is illustrated as followings.

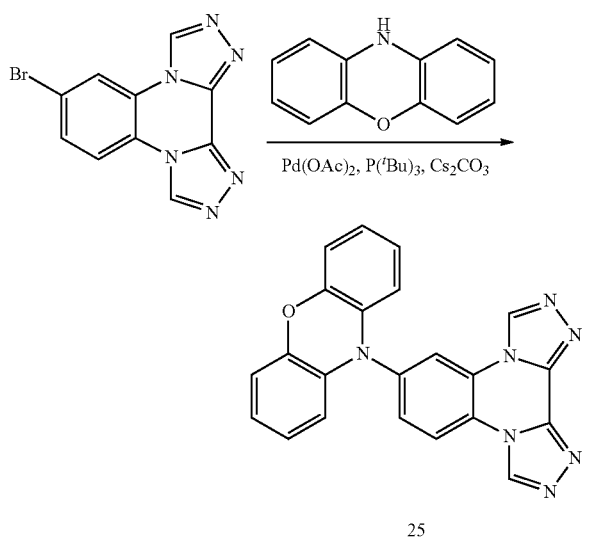

The starting precursor may be the intermediate 30-b (2.9 g, 10 mmol). 9,9-dimethylcarbazine may be substituted by phenoxazine; and the corresponding equivalents may be changed. Other precursors and process conditions may be similar to those of the embodiment 16 (compound 30). After the synthesis process, the solid compound 25 (1.9 g, yield 49%) may be obtained.

An LC-MS method may be used to analyze the final product (the obtained compound 25). The ESI-MS (m/z) of the final product is approximately 390.20 [M+H]$^+$. Such a value corresponds to the molecular weight of the compound 25.

Embodiment 18 describes the synthesis route and the synthesis process of the compound 12. The starting precursor may be the intermediate 22-a (0.57 g, 1.0 mmol). 1-bromobenzene may be substituted by a dehydrate THF solution of 1-bromomethane (50%) (0.95 g, 0.57 mmol); and the corresponding equivalents may be changed. Other precursors and process conditions may be similar to those of the embodiment 15 (compound 22). After the synthesis process, the solid compound 12 (0.19 g, yield 32%) may be obtained.

An LC-MS method may be used to analyze the final product (the obtained compound 12). The ESI-MS (m/z) of the final product is approximately 599.1 [M+H]$^+$. Such a value corresponds to the molecular weight of the compound 12.

Figure 6:
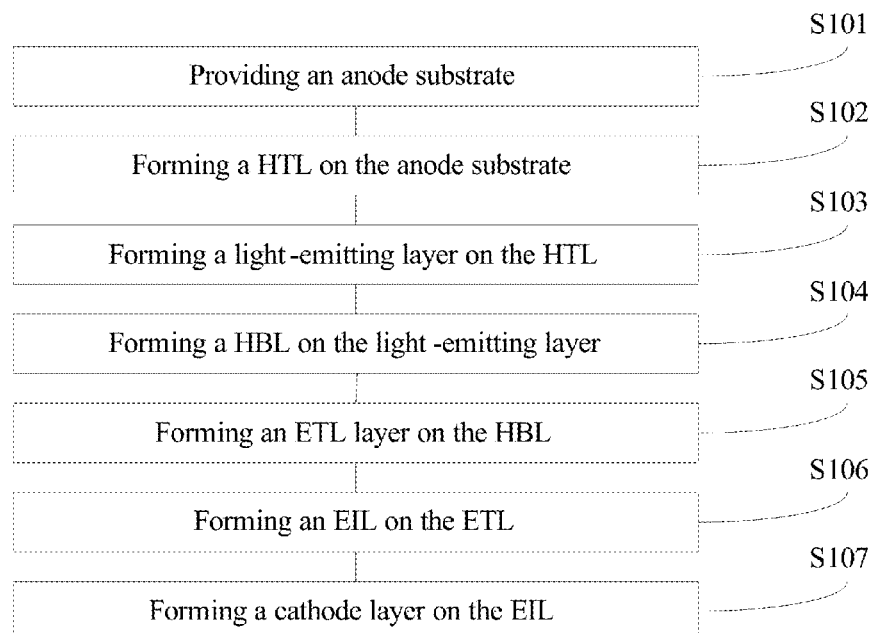
FIG. 6 illustrate an exemplary fabrication process of an organic photoelectric apparatus consistent with the disclosed embodiments.

FIG. 6 illustrates an exemplary fabrication process of the photoelectric apparatus having the disclosed compound consistent with the disclosed embodiments. Embodiments 19-30 describe the exemplary fabrication processes of organic photoelectric apparatus consistent with the disclosed embodiments. Control embodiments 1-2 describe fabrication processes of two control organic photoelectric apparatus.

FIG. 6 illustrates an exemplary fabrication process of the organic photoelectric apparatus having the disclosed compound. As shown in FIG. 6, the method includes providing an anode substrate (S101); forming a HTL on the anode substrate (S102); forming a light-emitting layer on the HTL using at least one disclosed compound (S103); forming a HBL on the light-emitting layer (S104); forming an ETL on the HBL (S105); forming an EIL on the ETL (S106); and forming a cathode layer on the EIL (S107). For illustrative purposes, the disclosed compounds will be used as the host material of one or more of the organic layers in the embodiments 19-24; and used as co-doping material in the embodiments 25-30.

Specifically, in the embodiment 19, an anode substrate having an ITO film with a thickness of 100 nm may be provided. The anode substrate having the ITO film may be sequentially cleaned by DI water, acetone and isopropanol alcohol in an ultrasound bath; and may be put into an oven. After a 30 minute surface treatment, the cleaned anode substrate may be transferred to a vacuum evaporation chamber. The plurality of layers the photoelectric apparatus may be deposited at a pressure approximately $2 \times 10^{-6}$ Pa. An N,N'-Bis-(1-naphthalenyl)-N,N'-bis-phenyl-(1,1'-biphenyl)-4,4'-diamine (a-NPD) layer with a thickness of 60 nm may be deposited on the ITO film; and a 4,4',4''-Tris(carbazol-9-yl)-triphenylamine (TCTA) layer with a thickness of 10 nm may be deposited on the NPD layer. The NPD layer and the TCTA layer may form the HTL. Further, the light-emitting layer with a thickness of 30 nm may be deposited on the HTL. The light-emitting layer may include the disclosed compound 1 as the host material (94 wt %) and Ir(ppy)₃ as the blue phosphorescence doping material (6 wt %). The host material and the doping material may be deposited simultaneously. Further, a bis(2-methyl-8-quinolinolato-N1,O8)-(1,1'-Biphenyl-4-olato)aluminum (BAlq) layer with a thickness of 5 nm may be deposited on the light-emitting layer to be used as the HBL. Then, a 4,7-diphenyl-1,10-phenanthroline (BPhen) layer with a thickness of 20 nm may be deposited on the HBL to be used as the ETL. Then, a LiF layer with a thickness of 1 nm may be deposited on the ETL to be used as the EIL. Then, an Al layer with a thickness of the 100 nm may be deposited on the EIL to be used as a cathode layer. Thus, the organic photoelectric apparatus may have a structure of ITO (100 nm)/NPD (60 nm)/TCTA (10 nm)/Ir(ppy)₃:91 (6 wt %, 30 nm)/BAlq (5 nm)/Bphen (20 nm)/LiF (1 nm)/Al (100 nm).

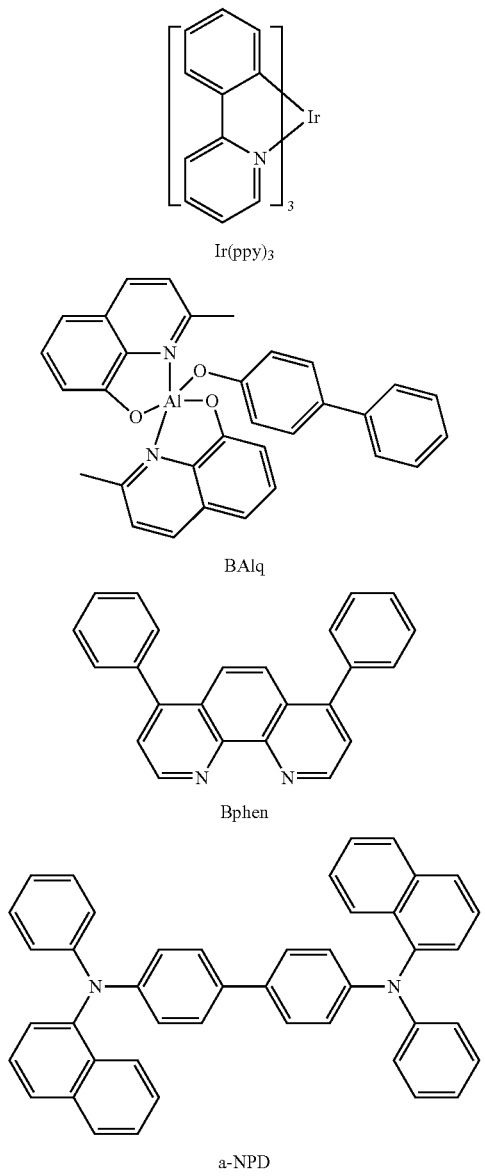

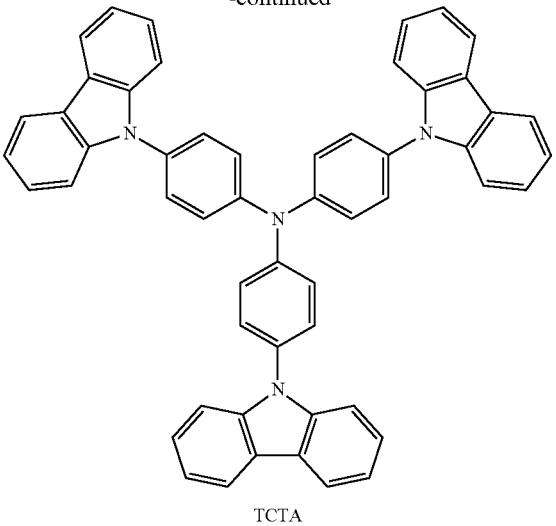

TCTA

In the embodiment 20, the disclosed compound 5 may be used to substitute the compound 1 described in the embodiment 19 as the host material. Other structures and steps may be similar to those described in the embodiment 19.

In the embodiment 21, the disclosed compound 12 may be used to substitute the compound 1 described in the embodiment 19 as the host material. Other structures and steps may be similar to those described in the embodiment 19.

In the embodiment 22, the disclosed compound 22 may be used to substitute the compound 1 described in the embodiment 19 as the host material. Other structures and steps may be similar to those described in the embodiment 19.

In the embodiment 23, the disclosed compound 25 may be used to substitute the compound 1 described in the embodiment 19 as the host material. Other structures and steps may be similar to those described in the embodiment 19.

In the embodiment 24, the disclosed compound 30 may be used to substitute the compound 1 described in the embodiment 19 as the host material. Other structures and steps may be similar to those described in the embodiment 19.

In the control embodiment 1, the compound CBP is used to substitute the compound 1 described in the embodiment 19 as the host material. Other structures and steps may be similar to those described in the embodiment 19.

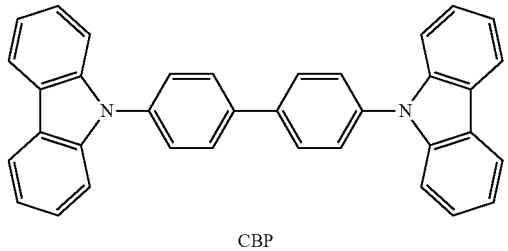 [SMILES: c1ccc2c(c1)c1ccccc1n2-c1ccc(-c2ccc(-n3c4ccccc4c4ccccc43)cc2)cc1 ; "CBP"]

CBP

In the embodiment 25, TBPe(1 wt %) may be used as the doping material; and the disclosed compound 1 (15 wt %) may be used as a co-doping material. DPEPO (84 wt % may be used as the host material. The TBPe, the disclosed compound 1 and the DPEPO may be deposited simultaneously to be used as the light-emitting layer with a thickness of approximately 30 nm. Other structures and steps may be similar to those described in the embodiment 19.

That is, the organic photoelectric apparatus may have a structure of ITO (100 nm)/NPD (60 nm)/TCTA (10 nm)/TBPe:1:DPEPO (1 wt %:15%, 30 nm)/BAlq (5 nm)/Bphen (20 nm)/LiF (1 nm)/Al (100 nm).

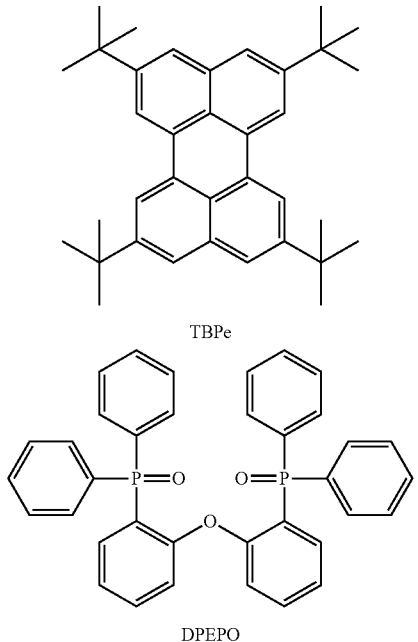

TBPe

DPEPO

In the embodiment 26, the disclosed compound 5 may be used to substitute the compound 1 described in the embodiment 25 as the co-doping material. Other structures and steps may be similar to those described in the embodiment 25.

In the embodiment 27, the disclosed compound 12 may be used to substitute the compound 1 described in the embodiment 25 as the co-doping material. Other structures and steps may be similar to those described in the embodiment 25.

In the embodiment 29, the disclosed compound 21 may be used to substitute the compound 1 described in the embodiment 25 as the co-doping material. Other structures and steps may be similar to those described in the embodiment 25.

In the embodiment 30, the disclosed compound 30 may be used to substitute the compound 1 described in the embodiment 25 as the co-doping material. Other structures and steps may be similar to those described in the embodiment 25.

In the control embodiment 2, TBPe (1 wt %) is used as the doping material; and DPEPO is used as the host material. TBPe and DPEPO are deposited simultaneously to be used as the light-emitting layer with a thickness of 30 nm. Other structures and steps may be similar to those described in the embodiment 25

The performance of the photoelectric apparatus described in the embodiments 19-30 and the control embodiments 1-2 may be evaluated from any aspects, and by any appropriate methods.

In one embodiment, the current of the photoelectric apparatus described in the embodiments 19-30 and the control embodiments 1-2 varying with the voltage is measured by a Keithley 2365A nanovoltagemeter. The current densities of the organic photoelectric apparatus at different voltages are obtained by dividing the current with the light-emitting area.

The brightness and the radiant energy flow density of the photoelectric apparatus described in the embodiments 19-30 and the control embodiments 1-2 at different voltages may be measured by a Konicaminolta CS-2000 Spectroradiometer. According to the brightness and the radiant energy of the photoelectric apparatus at different voltages, the current efficiency (Cd/A) and the external quantum efficiency EQE at a same current density (10 mA/cm$^2$) may be obtained.

The testing results of the photoelectric apparatus described in embodiments 19-24 and the control embodiment 1 are illustrated in Table 2. The testing results of the photoelectric apparatus described in embodiments 25-30 and the control embodiment 2 are illustrated in Table 3.

TABLE 2

Testing results corresponding to different host materials

| | Voltage (V) | Current efficiency (Cd/A) | EQE | CIE |
|---|---|---|---|---|
| Embodiment 19 | 4.8 | 42.3 | 16.1 | green |
| Embodiment 20 | 4.7 | 45.1 | 16.7 | green |
| Embodiment 21 | 4.8 | 42.8 | 16.1 | green |
| Embodiment 22 | 4.8 | 41.9 | 16.0 | green |
| Embodiment 23 | 4.6 | 45.8 | 16.8 | green |
| Embodiment 24 | 4.6 | 47.3 | 17.3 | green |
| Control embodiment 1 | 5.1 | 40.3 | 15.6 | green |

TABLE 3

Testing results corresponding to different co-doping materials

| | Voltage (V) | Current efficiency (Cd/A) | EQE | CIE |
|---|---|---|---|---|
| Embodiment 25 | 7.5 | 3.2 | 2.2 | blue |
| Embodiment 26 | 7.4 | 3.4 | 2.5 | blue |
| Embodiment 27 | 7.5 | 3.4 | 2.3 | blue |
| Embodiment 28 | 7.7 | 3.0 | 1.9 | blue |
| Embodiment 29 | 7.3 | 3.7 | 2.7 | blue |
| Embodiment 30 | 7.4 | 3.3 | 2.2 | blue |
| Control embodiment 2 | 8.1 | 1.4 | 0.8 | blue |

According to table 2 and table 3, under a same current density (10 mA/cm$^2$), comparing with the photoelectric apparatus described in the control embodiments 1-2, the photoelectric apparatus described in the embodiments 19-30, which have the disclosed compounds as host material or co-doping material, may have lower drive voltages, higher current efficiencies, and higher external quantum efficiencies. That is, the organic photoelectric apparatus having the disclosed compounds may have better performance. Thus, the disclosed compounds may be used as the host materials, and/or the co-doping materials of the organic layers of the photoelectric apparatus.

The above detailed descriptions only illustrate certain exemplary embodiments of the present invention, and are not intended to limit the scope of the present invention. Those skilled in the art can understand the specification as whole and technical features in the various embodiments can be combined into other embodiments understandable to those persons of ordinary skill in the art. Any equivalent or modification thereof, without departing from the spirit and principle of the present invention, falls within the true scope of the present invention.

What is claimed is:

1. A nitrogen-containing heterocyclic compound having a general formula (I):

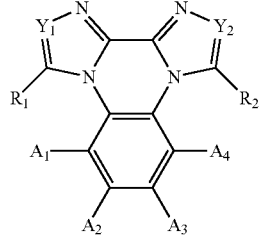
(I)

wherein $A_1$, $A_2$, $A_3$, and $A_4$ are independently selected from a hydrogen atom, and a functional group having a general formula (II); $A_1$, $A_2$, $A_3$, and $A_4$ include at least one functional group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N, the general formula (II) being:

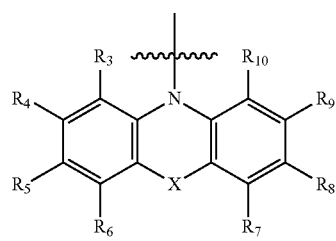
(II)

wherein X is selected from one of oxyl group (—O—), sulfhydryl group (—S—), substituted or non-substituted imino group, substituted or non-substituted methylene group, and substituted or non-substituted silicylene group; and $R_3$, $R_4$, $R_5$, $R_6$, $R_7$, $R_8$, $R_9$, and $R_{10}$ are independently selected from any one of hydrogen, deuterium, $C_{1-30}$ alkyl group, $C_{6-30}$ aromatic group, and $C_{2-30}$ heterocyclic aromatic group.

2. The nitrogen-containing heterocyclic compound according to claim 1, wherein:
an energy level difference ($\Delta E_{st}$) between a lowest singlet state $S_1$ and a lowest triplet state $T_1$ is smaller than or equal to approximately 0.30 eV.

3. The nitrogen-containing heterocyclic compound according to claim 1, wherein the compound having the general formula (II) comprises one of:
—O—, —S—, —CH$_2$—, —C(CH$_3$)$_2$—, —CH(CH$_3$)—,

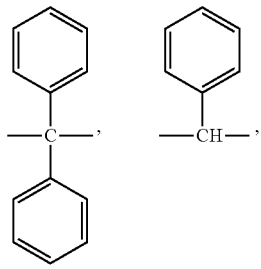

—SiH$_2$—, —Si(CH$_3$)$_2$—, —SiH(CH$_3$)—,

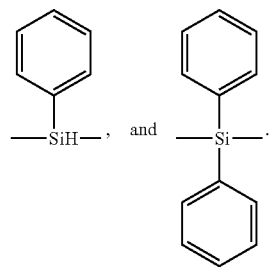
and

4. The nitrogen-containing heterocyclic compound according to claim 1, wherein:
$R_3$, $R_4$, $R_5$, $R_6$, $R_7$, $R_8$, $R_9$ and $R_{10}$ are all hydrogen.

5. The nitrogen-containing heterocyclic compound according to claim 1, wherein the compound having the general formula (II) is one of:

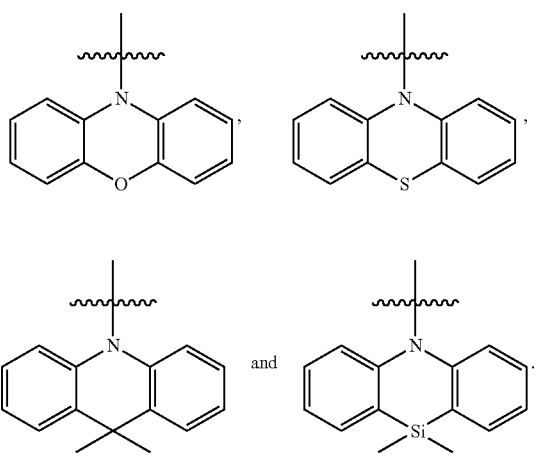

6. The nitrogen-containing heterocyclic compound according to claim 1, comprising one of:

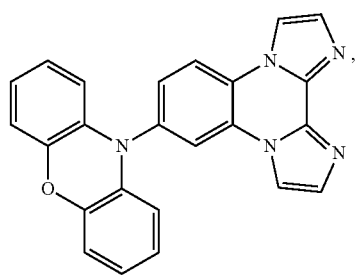

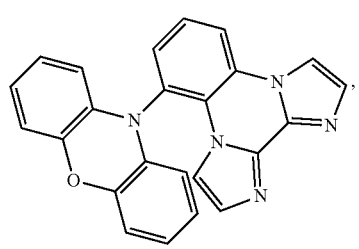

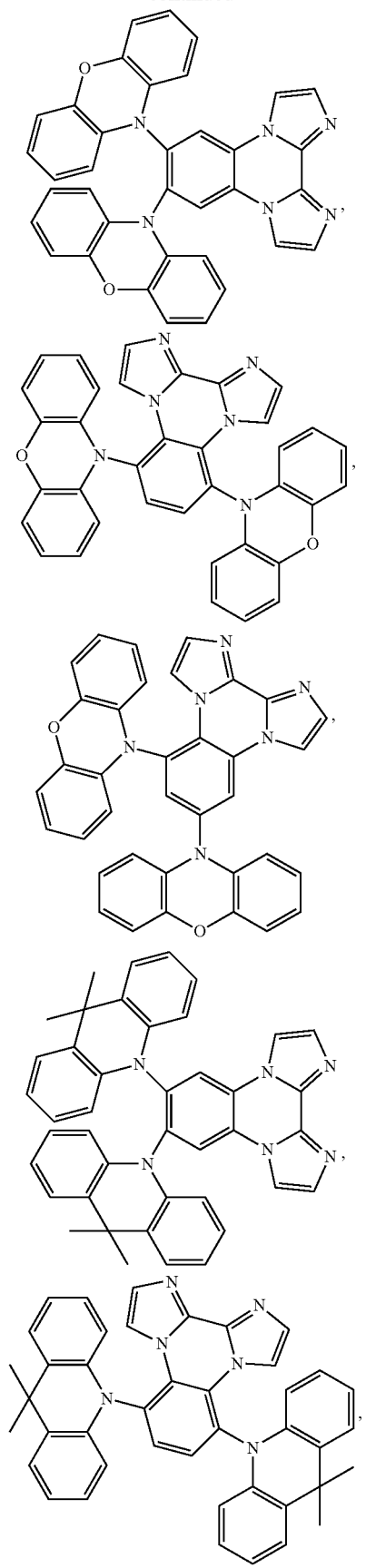
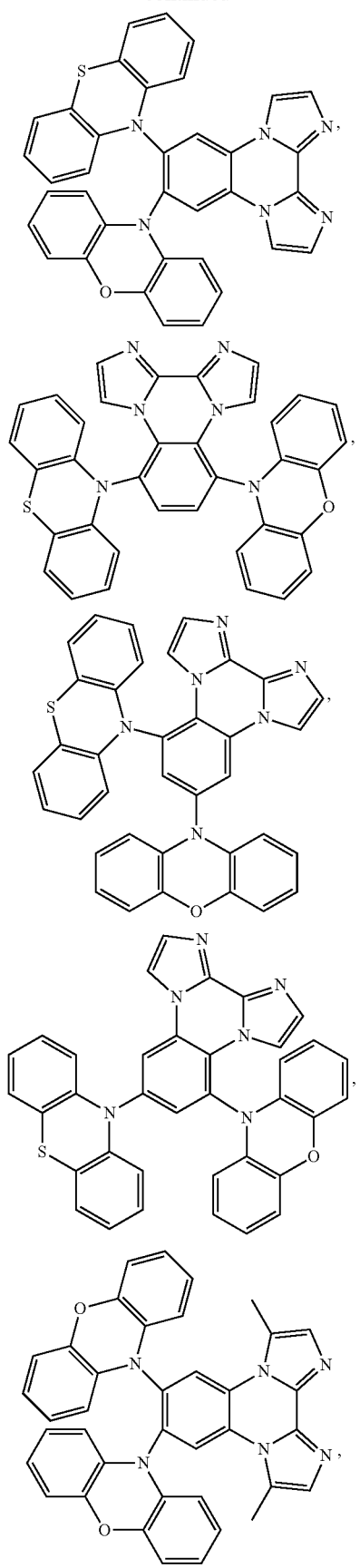

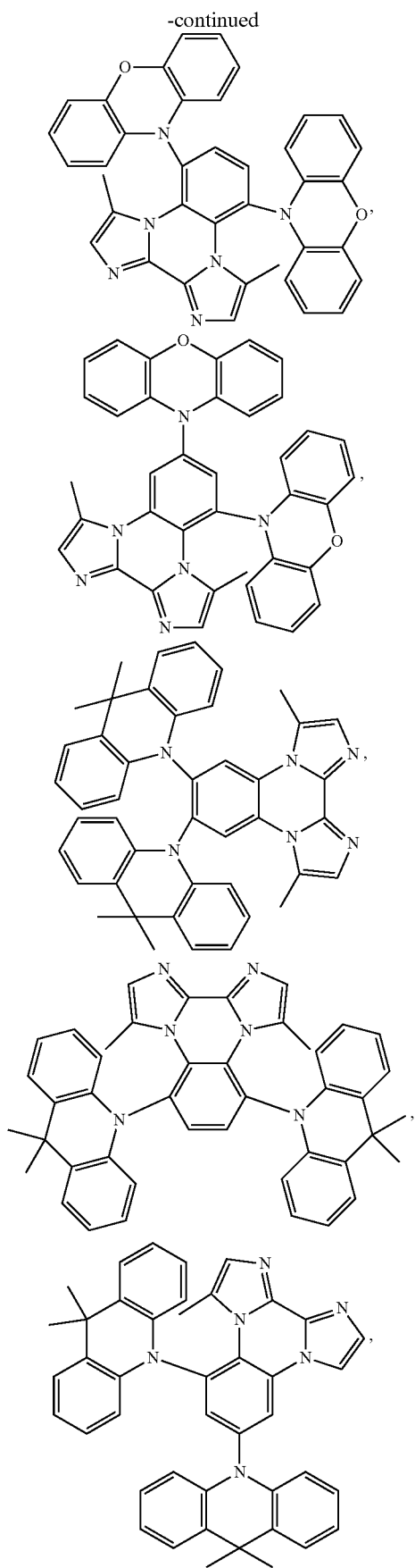
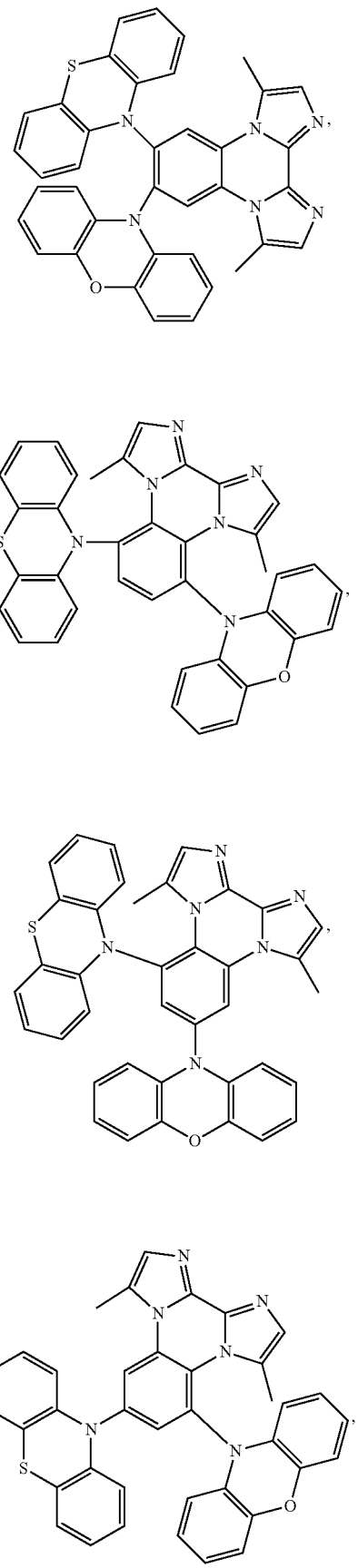

47
-continued
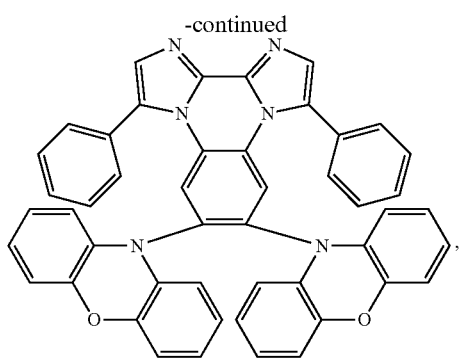
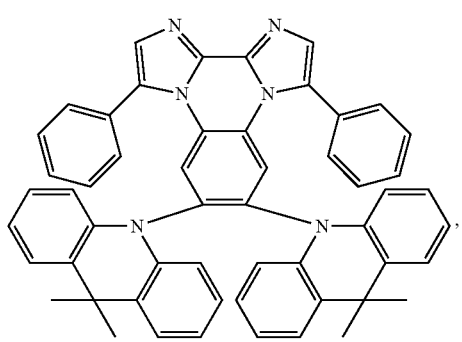
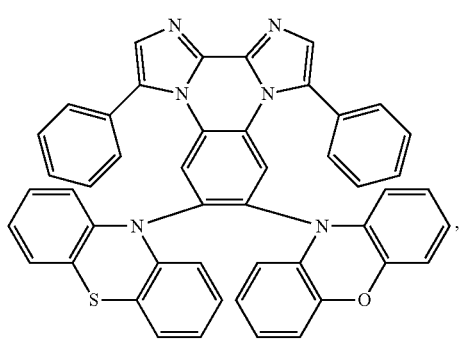
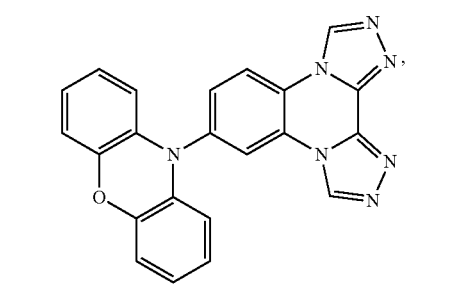
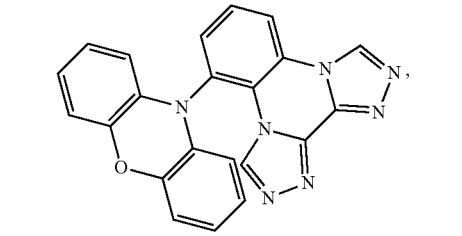
48
-continued
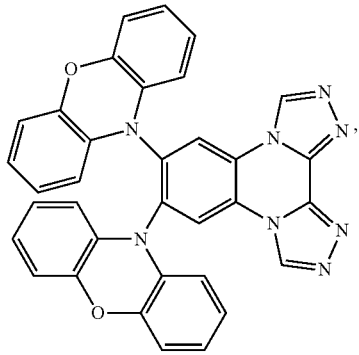
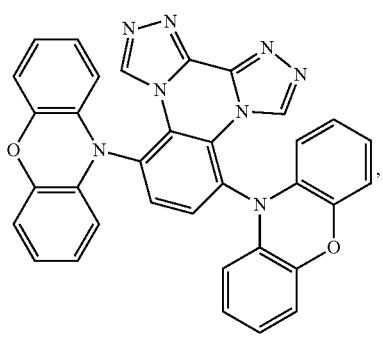
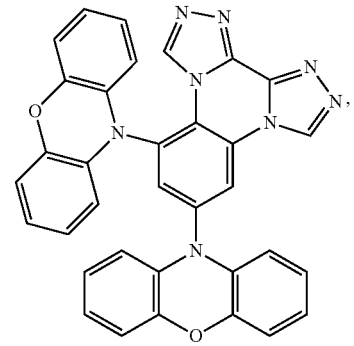
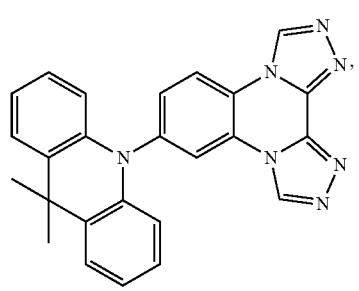
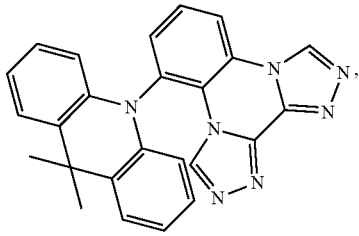

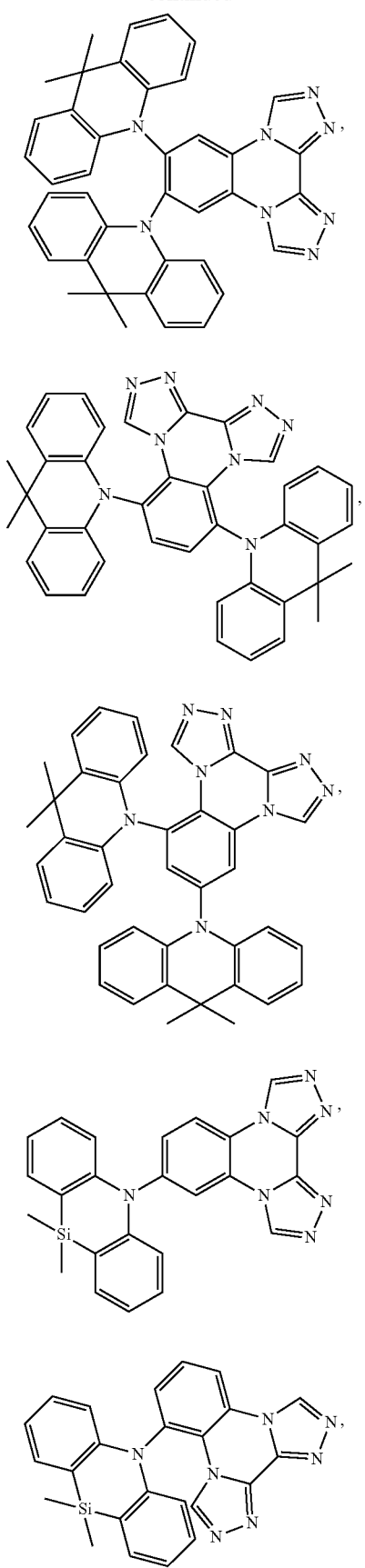
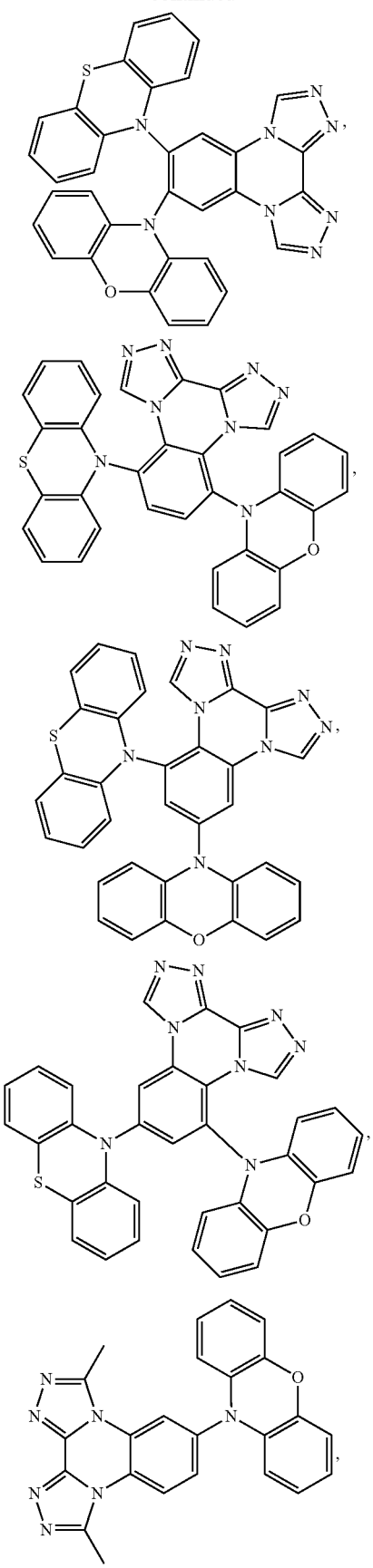

51
-continued
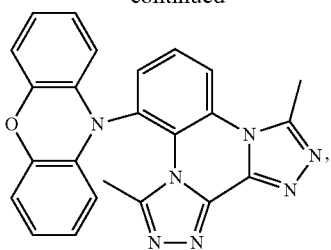
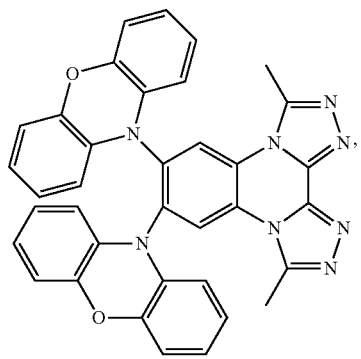
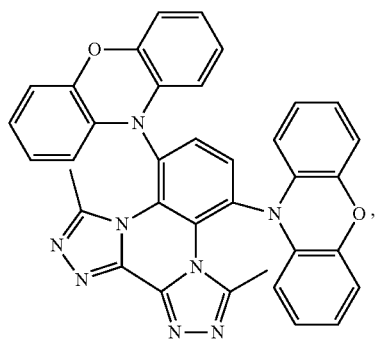
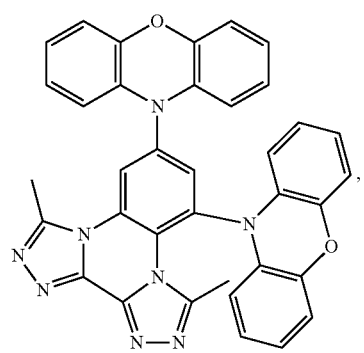
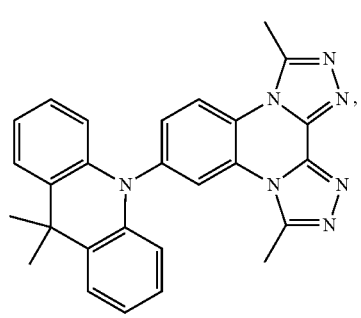
52
-continued
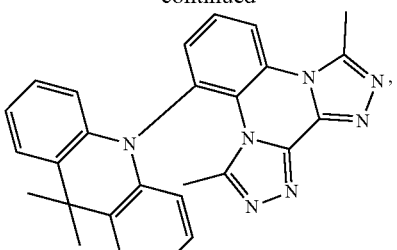
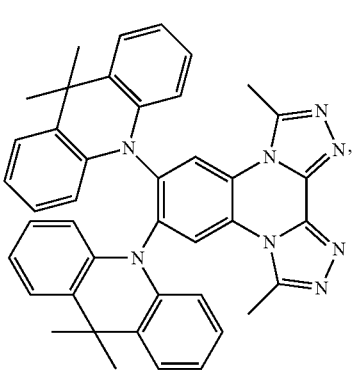
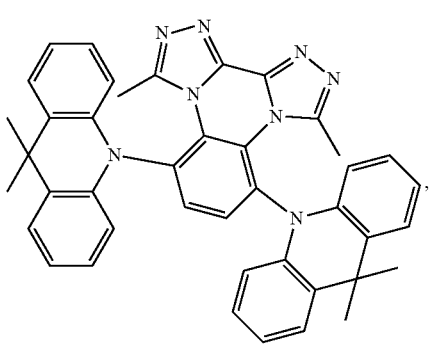
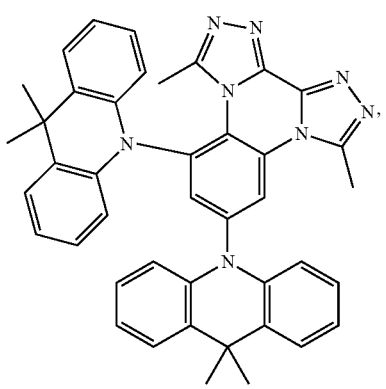
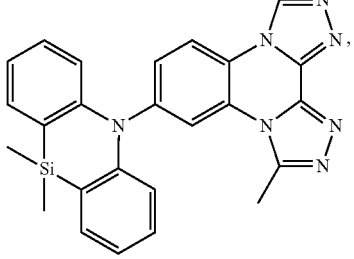

53
-continued
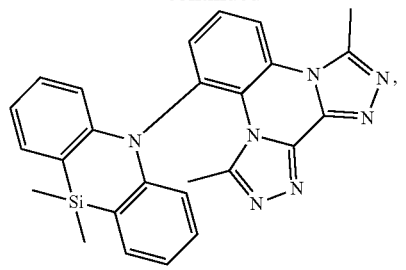
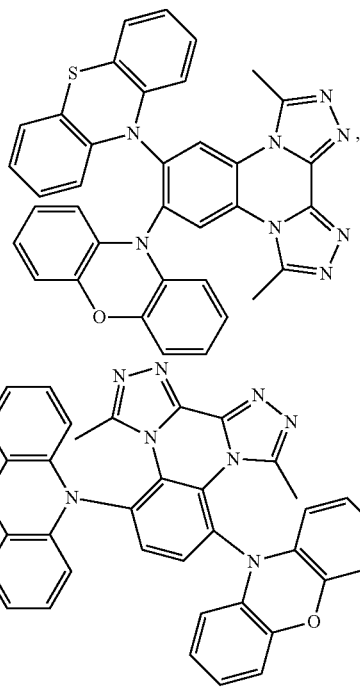
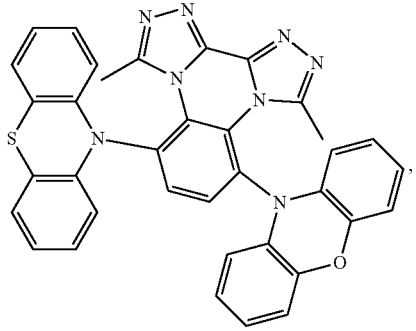
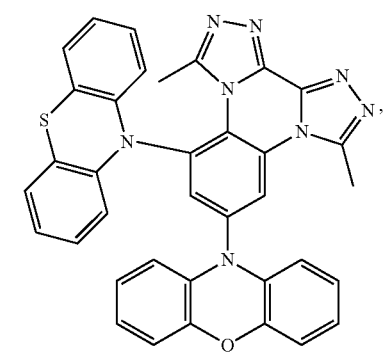
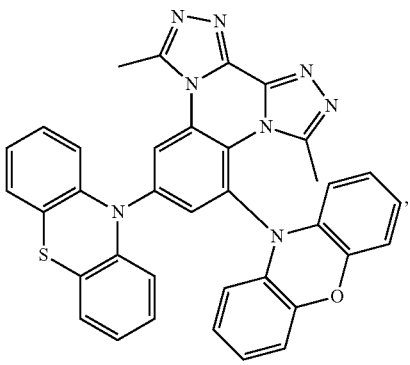
54
-continued
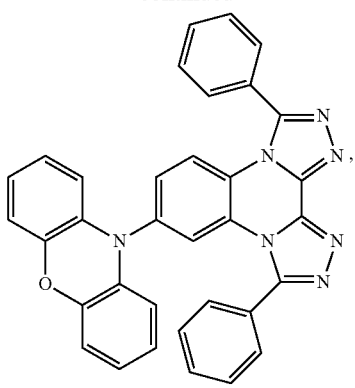
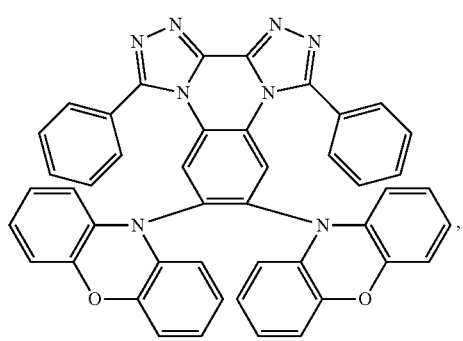
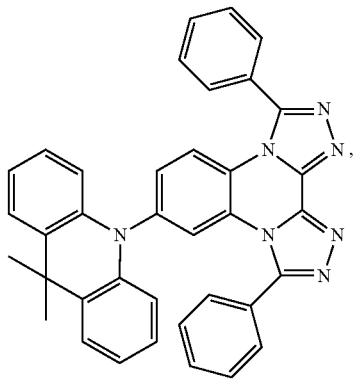
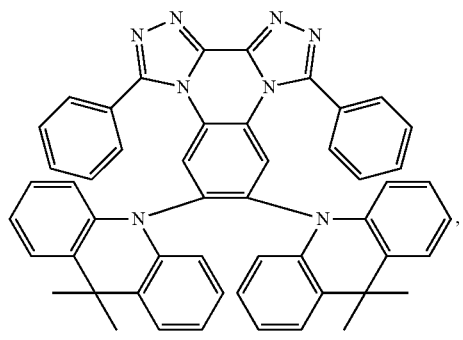

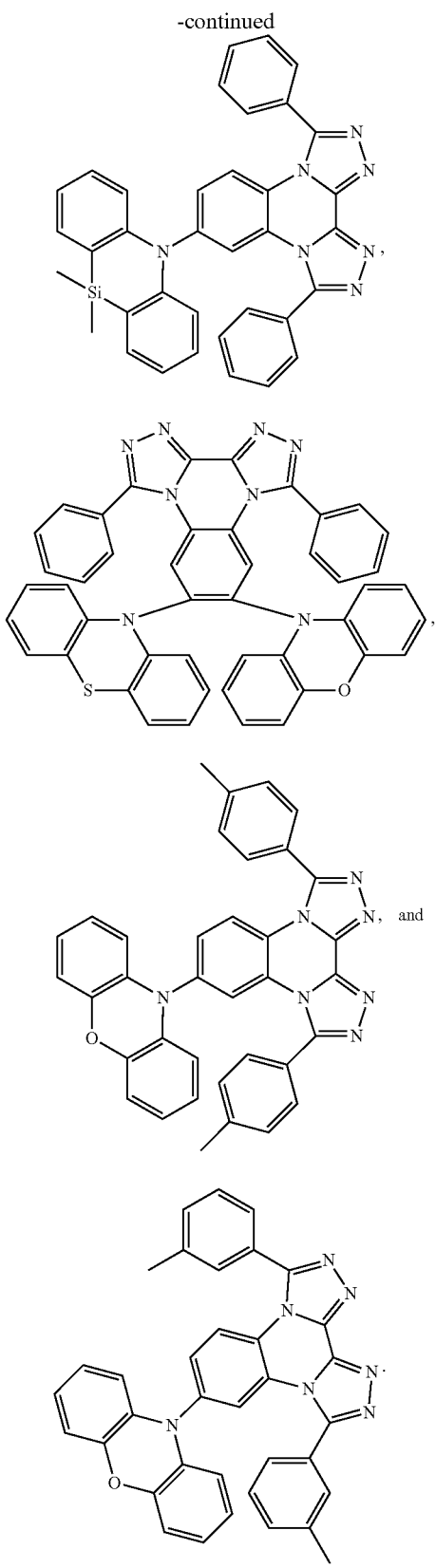

7. The nitrogen-containing heterocyclic compound according to claim 1, comprising:
a thermally activated delayed fluorescence performance.

8. An organic photoelectric apparatus, comprising:
an anode substrate;
at least one organic layer formed over the anode substrate; and
a cathode layer formed over the organic layer,
wherein the at least one organic layer includes at least one nitrogen-containing heterocyclic compound having a general formula (I):

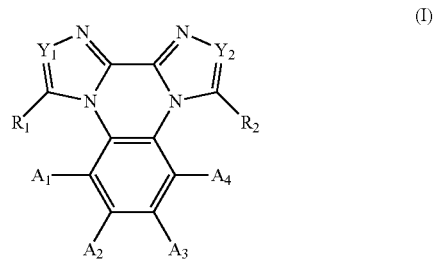

(I)

wherein $A_1$, $A_2$, $A_3$, and $A_4$ are independently selected from a hydrogen atom, a functional group having a general formula (II); $A_1$, $A_2$, $A_3$, and $A_4$ include at least one functional group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N, the general formula (II) being:

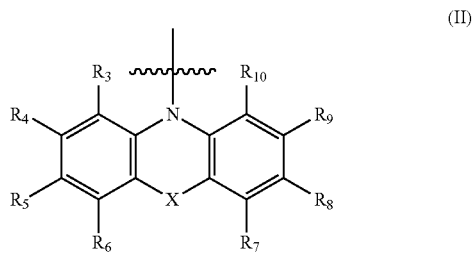

(II)

wherein X is selected from one of oxyl group (—O—), sulfhydryl group (—S—), substituted or non-substituted imino group, substituted or non-substituted methylene group, and substituted or non-substituted silicylene group; and $R_3$, $R_4$, $R_5$, $R_6$, $R_7$, $R_8$, $R_9$, and $R_{10}$ are independently selected from any one of hydrogen, deuterium, $C_{1-30}$ alkyl group, $C_{6-30}$ aromatic group, and $C_{2-30}$ heterocyclic aromatic group.

9. The organic photoelectric apparatus according to claim 8, wherein the organic layer comprises:
at least one light-emitting layer; and
the at least one light-emitting layer includes one or at least two nitrogen-containing heterocyclic compounds.

10. The organic photoelectric apparatus according to claim 9, wherein:
the one or at least two nitrogen-containing heterocyclic compounds are used as one of a host material, a doping material, and a co-doping material of the at least one light-emitting layer.

11. The organic photoelectric apparatus according to claim 9, wherein the organic layer further comprises:
one or at least two of a hole transport layer, a hole injection layer, a hole barrier layer, an electron transport layer, an electron injection layer and an electron barrier layer.

12. The organic photoelectric apparatus according to claim 11, wherein:
the nitrogen-containing heterocyclic compound is a host material of the at least one light-emitting layer.

13. The organic photoelectric apparatus according to claim 8, wherein:
an energy level difference ($\Delta E_{st}$) among a lowest singlet state $S_1$ and a lowest triplet state $T_1$ of the nitrogen-containing heterocyclic compound is smaller than or equal to approximately 0.30 eV.

14. The organic photoelectric apparatus according to claim 8, wherein:
the nitrogen-containing heterocyclic compound has a thermally activated delayed fluorescence performance.

15. A method for fabricating an organic photoelectric apparatus, comprising:
providing an anode substrate,
forming at least one organic layer over the anode substrate; and
forming a cathode layer over the organic layer,
wherein the at least one organic layer includes at least one nitrogen-containing heterocyclic compound having a general formula (I):

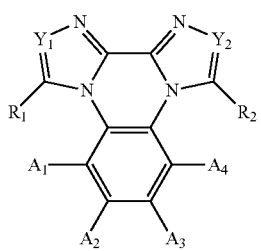

(I)

wherein $A_1$, $A_2$, $A_3$, and $A_4$ are independently selected from a hydrogen atom, a functional group having a general formula (II); $A_1$, $A_2$, $A_3$, and $A_4$ include at least one functional group having the general formula (II); $R_1$ and $R_2$ are independently selected from one of hydrogen, deuterium, $C_{1-30}$ alkyl group, $C_{6-30}$ aromatic group and $C_{2-30}$ heterocyclic aromatic group; $Y_1$ and $Y_2$ are independently selected from substituted or non-substituted C and N
the general formula (II) being:

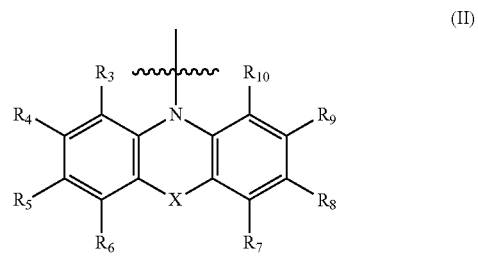

(II)

wherein X is selected from one of oxyl group (—O—), sulfhydryl group (—S—), substituted or non-substituted imino group, substituted or non-substituted methylene group, and substituted or non-substituted silicylene group; and $R_3$, $R_4$, $R_5$, $R_6$, $R_7$, $R_8$, $R_9$, and $R_{10}$ are independently selected from any one of hydrogen, deuterium, $C_{1-30}$ alkyl group, $C_{6-30}$ aromatic group, and $C_{2-30}$ heterocyclic aromatic group.

16. The method according to claim 15, wherein:
the organic layer comprises at least one light-emitting layer; and
the at least one light-emitting layer includes one or at least two nitrogen-containing heterocyclic compounds.

17. The method according to claim 15, wherein:
the one or at least two nitrogen-containing heterocyclic compounds are used as one of a host material, a doping material, and a co-doping material of the at least one light-emitting layer.

18. The method according to claim 15, wherein forming the at least one organic layer further comprises:
forming a hole transport layer on the anode substrate;
forming a light-emitting layer on the hole transport layer;
forming a hole barrier layer on the light-emitting layer;
forming an electron transport layer on the hole barrier layer; and
forming an electron injection layer on the electron transport layer.

19. The method according to claim 15, wherein:
the organic layer is formed by an evaporation process.

20. The method according to claim 15, wherein:
the nitrogen-containing heterocyclic compound has a thermally activated delayed fluorescence performance.

* * * * *